(12) United States Patent
Tabassum et al.

(10) Patent No.: US 10,053,480 B1
(45) Date of Patent: Aug. 21, 2018

(54) ANTI-QUORUM AND DNA CLEAVING AGENT

(71) Applicant: KING SAUD UNIVERSITY, Riyadh (SA)

(72) Inventors: Sartaj Tabassum, Riyadh (SA); Hamad A. Al-Lohedan, Riyadh (SA); Hazem Ghabour, Riyadh (SA); Mohd Sajid Ali, Riyadh (SA); Rais Ahmad Khan, Riyadh (SA); Fohad Mabood Husain, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/730,637

(22) Filed: Oct. 11, 2017

(51) Int. Cl.
| | |
|---|---|
| *C07F 15/00* | (2006.01) |
| *A61K 31/555* | (2006.01) |
| *A61P 31/04* | (2006.01) |
| *C07K 14/525* | (2006.01) |
| *A61P 35/00* | (2006.01) |
| *C07K 14/47* | (2006.01) |

(52) U.S. Cl.
CPC ........ *C07F 15/0046* (2013.01); *A61K 31/555* (2013.01); *A61P 31/04* (2018.01); *A61P 35/00* (2018.01); *C07K 14/47* (2013.01); *C07K 14/525* (2013.01)

(58) Field of Classification Search
None
See application file for complete search history.

(56) References Cited

U.S. PATENT DOCUMENTS

| | | | |
|---|---|---|---|
| 6,979,681 B2 | 12/2005 | Morris et al. | |
| 7,691,418 B2 | 4/2010 | Roussel | |
| 2009/0318402 A1 | 12/2009 | Dougan et al. | |
| 2011/0319636 A1* | 12/2011 | Nordstrom | B01J 31/2265 548/537 |

FOREIGN PATENT DOCUMENTS

| | | |
|---|---|---|
| CN | 101747382 A | 6/2010 |
| CN | 103880890 A | 6/2014 |
| CN | 105601575 A | 5/2016 |

OTHER PUBLICATIONS

Berndsen RH, Weiss A, Abdul UK, Wong TJ, Meraldi P, Griffioen AW, Dyson PJ and Nowak-Sliwinska P, Combination of ruthenium(II)-arene complex [Ru(η6-p-cymene)Cl2(pta)] (RAPTA-C) and the epidermal growth factor receptor inhibitor erlotinib results in efficient angiostatic and antitumor activity, Scientific Reports, in press, 2017.

Ziga Ude, Isolda Romero-Canelón, Brendan Twamley, Deirdre Fitzgerald Hughes, Peter J. Sadler, Celine J. Marmion, A novel dual-functioning ruthenium(II)-arene complex of an anti-microbial ciprofloxacin derivative Anti-proliferative and anti-microbial activity Journal of Inorganic Biochemistry 160 (2016) 210-217.

Iztok Turel, Jakob Kljun, Franc Perdih, Elena Morozova, Vladimir Bakulev, Nina Kasyanenko, Jo Ann W. Byl, and Neil Osheroff. First Ruthenium Organometallic Complex of Antibacterial Agent Ofloxacin. Crystal Structure and Interactions with DNA, Inorganic Chemistry, 2010, 49, 10750-10752.

Farhana Aman, Muhammad Hanif, Waseeq Ahmad Siddiqui, Adna Ashraf, LukasK. Filak, Jóhannes Reynisson, Tilo Söhnel, Stephen M. F. Jamieson, and Christian G. Hartinger. Anticancer Ruthenium(η6-p-cymene) Complexes of Nonsteroida Anti-inflammatory Drug Derivatives, Organometallics, 2014, 33 (19), pp. 5546-5553.

Editorial of Special Issue Ruthenium Complex: The Expanding Chemistry of the Ruthenium Complexes Ileana Dragutan, Valerian Dragutan and Albert Demonceau, Molecules 2015, 20, 17244-17274.

Lauren K. Wareham, Robert K. Poole, and Mariana Tinajero-Trejo, CO-releasing Metal Carbonyl Compounds as Antimicrobial Agents in the Post-antibiotic Era Journal of Biological Chemistry, 2015, 290, 31.

Atakilt Abebe and Tizazu Hailemariam Synthesis and Assessment of Antibacterial Activities of Ruthenium(III) Mixed Ligand Complexes Containing 1,10-Phenanthroline and Guanide, Bioinorganic Chemistry and Applications, vol. 2016 (2016), Article ID 3607924, 9.

Yang XY, Zhang L, Liu J, Li N, Yu G, Cao K, Han J, Zeng G, Pan Y, Sun X, He QYProteomic analysis on the antibacterial activity of a Ru(II) complex against *Streptococcus pneumoniae*, J Proteomics. Feb. 6, 2015; 115:107-16.

Oxidative Stress and Antimicrobial Activity of Chromium(III) and Ruthenium(II) Complexes on *Staphylococcus aureus* and (Continued)

*Primary Examiner* — Bong-Sook Baek
(74) *Attorney, Agent, or Firm* — Richard C. Litman

(57) ABSTRACT

The anti-quorum and DNA cleaving agent is directed to a ruthenium complex formulated from dichloro-(η⁶-p-cymene) ruthenium(II) dimer and 2-chloroquinoxaline, the complex having the formula:

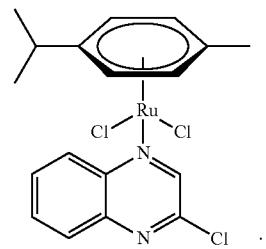

The reaction cleaves the dimer, leaving a half-sandwich ruthenium complex with an $\eta^6$ coordination bond to the arene ligand and an Ru—N bond attaching the chloroquinoxaline to the ruthenium complex. The agent has an anti-quorum sensing effect on bacteria, inhibiting the formation of biofilm and inhibiting bacterial virulence. The agent also binds to DNA and may cleave the DNA, e.g., at the N7 base pair of guanine, due to a hydrolytic mechanism, suggesting potential use as an anticancer or antitumor agent.

5 Claims, 20 Drawing Sheets

(56) References Cited

OTHER PUBLICATIONS

*Escherichia coli*, BioMed Research International vol. 2013 (2013), Article ID 906912, 7.

* cited by examiner

ANTI-QUORUM AND DNA CLEAVING AGENT

INCORPORATION BY REFERENCE OF MATERIAL SUBMITTED IN COMPUTER READABLE FORM

The Applicant hereby incorporates by reference the sequence listing contained in the ASCII text file titled "32903.08 Sequence Listing_ST25.txt," created Jan. 2, 2018 and having 1.0 KB of data.

BACKGROUND

1. Field

The disclosure of the present patent application relates generally to ruthenium coordination complexes useful as antibacterial and anticancer compounds, and particularly to an anti-quorum and DNA cleaving agent formulated from dichloro-($\eta^6$-p-cymene) ruthenium(II) dimer and 2-chloroquinoxaline.

2. Description of the Related Art

Recently, organo-ruthenium compounds have attracted considerable interest as antimicrobial agents. This is likely due to such properties of the organo-ruthenium compounds as low toxicity and efficacy against bacteria. For instance, an organometallic ruthenium (Ru) compound with chelating N-donor ligand systems was reported to undergo relatively fast hydrolysis. Further, complexes bearing an N-donor ligand have shown biological activity. Biological activity of the p-cymene Ru(II) complex has been investigated, and some of the compounds were shown to be potent protein kinase inhibitors. In addition, quinolones are synthetic antibacterial agents widely used in clinical practice.

By applying different techniques, the DNA interactions of the ruthenium compounds and the affinity to proteins of the ruthenium compounds have been studied. A recent report of the reactivity of a topoisomerase and DNA with quinolone complex shows the metal ion is coordinated by the quinolone, which, in turn, forms a hydrogen bond to coordinate bonds with DNA bases. As such, binding Ru(p-cymene) complexes with DNA or proteins has been established.

Furthermore, due to various biological properties of quinolones, quinones and other drug molecules, a series of compounds has been prepared and the corresponding interaction with DNA has been studied. Arene-Ru(II) compounds with scorpionate ligands with DNA binding has been investigated using various spectroscopic methods. The complexes exhibited high binding affinity under physiological condition. Thus, in vitro antitumor studies of the compounds were carried out on 15 cell lines and inhibitory activity with topoisomerase IIα was examined.

Further, the synthesis and characterization of Ru(II), a p-cymene complex of the next generation quinazoline nalidixic, acid cinoxacin, and comparisons of these analogous complexes have been reported. This has allowed determination of the corresponding stability in aqueous solution reactivity toward the DNA and the serum transport protein human serum albumin.

Moreover, ruthenium-based anticancer drugs have been shown to display low general toxicity and to specifically accumulate in cancer cells, and similarly, in bacterial cells. The transport protein, transferrin, facilitated more intake of iron for essential cellular processes. The iron-mimicking feature of ruthenium compounds accumulates in bacterial cells. In addition, ruthenium-arene complexes provide an ideal ruthenium scaffold to deliver to bacterial cells because they provide a proper lipophilicity for transport through cell membranes. The ruthenium compounds either form hydrogen bonds to the nucleobases through the nitrogen of the drug moiety or may bind to the phosphate backbone of the DNA.

Organometallic ruthenium complex of ofloxacin antibacterial agent ([($\eta^6$-p-cymene) RuCl(O, O-oflo)]·2.8H$_2$O), which has been synthesized and characterized by X-Ray crystallography. In this "piano-stool" complex, quinolone is bidentate-coordinated to the metal through the ring carbonyl and one of the carboxylic oxygen atoms. Because interactions have been observed only in a solution with low ionic strengths, it has been further established that the electrostatic attraction between the ruthenium complex and DNA in a solution is important for binding. AFM (atomic force microscopy) has shown that the compound provokes DNA shrinkage at low concentration.

However, in spite of the advances that have been made, there is still a need for pharmaceutical compounds that disrupt bacterial quorum sensing to inhibit the formation of biofilm and bacterial virulence, as well as anti-tumor compounds. Thus, an anti-quorum and DNA cleaving agent solving the aforementioned problems is desired.

SUMMARY

The anti-quorum and DNA cleaving agent is directed to a ruthenium complex formulated from dichloro-($\eta^6$-p-cymene) ruthenium(II) dimer and 2-chloroquinoxaline, the complex having the formula:

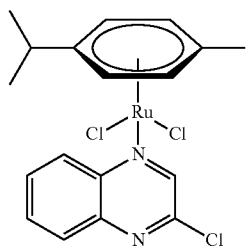

The reaction cleaves the dimer, leaving a half-sandwich ruthenium complex with an $\eta^6$ coordination bond to the arene ligand and an Ru—N bond attaching the chloroquinoxaline to the ruthenium complex. The agent has an anti-quorum sensing effect on bacteria, inhibiting the formation of biofilm and inhibiting bacterial virulence. The agent also binds to DNA and may cleave the DNA, e.g., at the N7 base pair of guanine, due to a hydrolytic mechanism, suggesting potential use as an anticancer or antitumor agent.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The anti-quorum and DNA cleaving agent is directed to a ruthenium complex formulated from dichloro-($\eta^6$-p-cymene) ruthenium(II) dimer and 2-chloroquinoxaline, the complex having the formula:

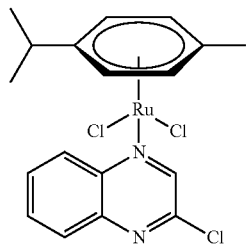

The reaction cleaves the dimer, leaving a half-sandwich ruthenium complex with an $\eta^6$ coordination bond to the arene ligand and an Ru—N bond attaching the chloroquinoxaline to the ruthenium complex. The agent has an anti-quorum sensing effect on bacteria, inhibiting the formation of biofilm and inhibiting bacterial virulence. The agent also binds to DNA and may cleave the DNA, e.g., at the N7 base pair of guanine, due to a hydrolytic mechanism, suggesting potential use as an anticancer or antitumor agent.

A new metal-based drug containing dichloro($\eta^6$-p-cymene)ruthenium(II) and a 2-chloroquinoxaline drug moiety was designed, synthesized, and characterized by spectroscopic methods. The spectroscopic methods included FT-IR, UV-vis, FL, NMR spectroscopy, and X-ray crystallography. To ascertain the biological activity, the interaction of the potential drug molecule firm structure was docked on different biomolecules, such as protein and DNA, by molecular modeling studies. This also provided the opportunity to find the site of action and bond strength of the drug to the biomolecule on the basis of thermodynamic parameters.

The docking results were further validated by in vitro binding studies of the drug moiety with proteins. The in vitro binding studies included UV-VIS, fluorescence spectrophotometric studies, and CD spectroscopy. Binding parameters were calculated. Further, anti-quorum activity was also performed to determine industrial application of the compound as an anti-bacterial in the pharmaceutical and agricultural industries. On the basis of the computational biology output, wet lab experiments, and in vitro studies, the compound shows high pharmaceutical potential and may be a next generation anti-quorum agent for bacterial-resistant chronic diseases.

Figure 1A:
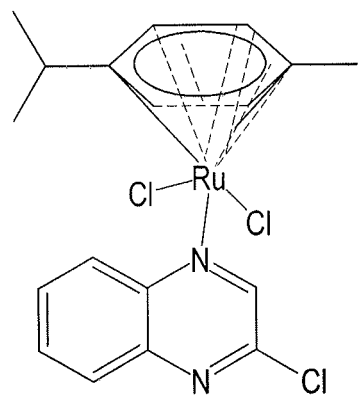
FIG. 1A is a graphical drawing of the structural formula of the anti-quorum and DNA cleaving agent, also referred to herein as the RAQA (ruthenium anti-quorum agent) complex.
Figure 1B:
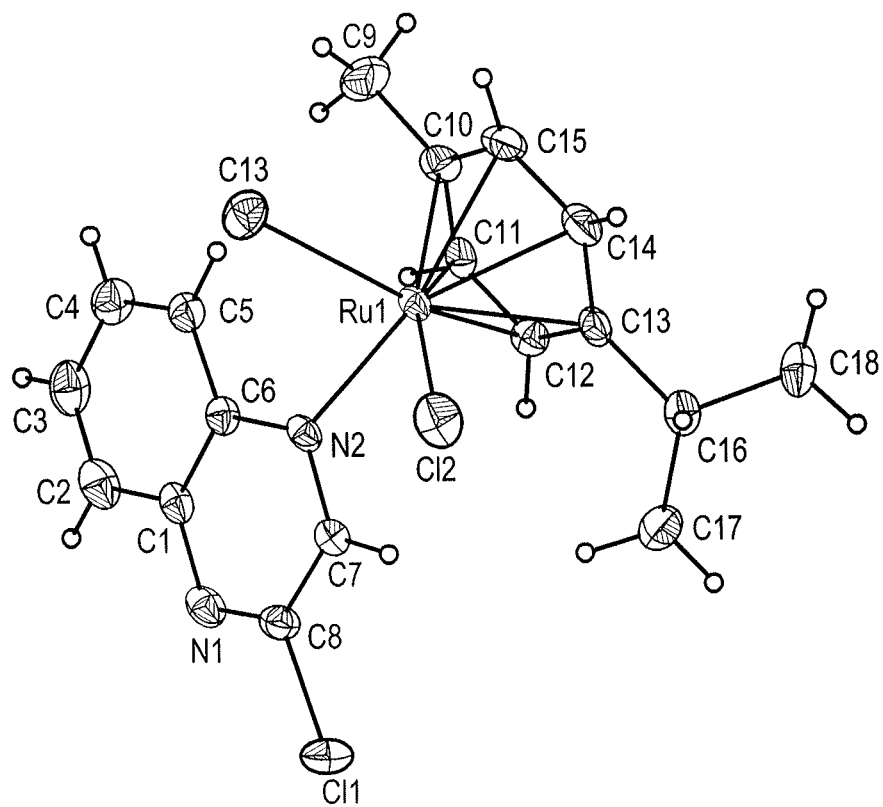
FIG. 1B is an ORTEP view of the RAQA complex.
Figure 2:
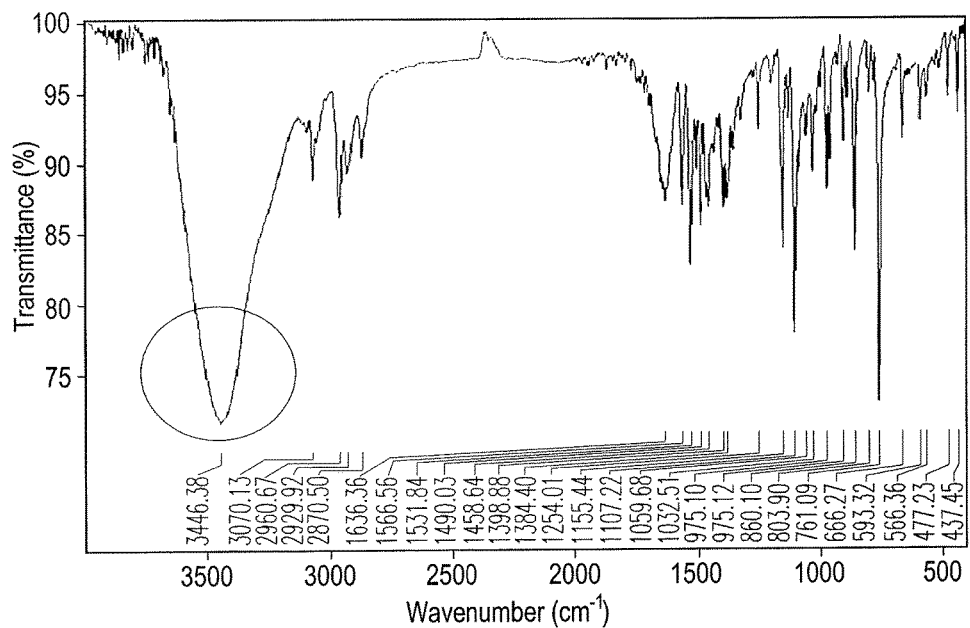
FIG. 2 is the FT-IR spectrum of the anti-quorum and DNA cleaving agent of FIG. 1A.
Figure 3:
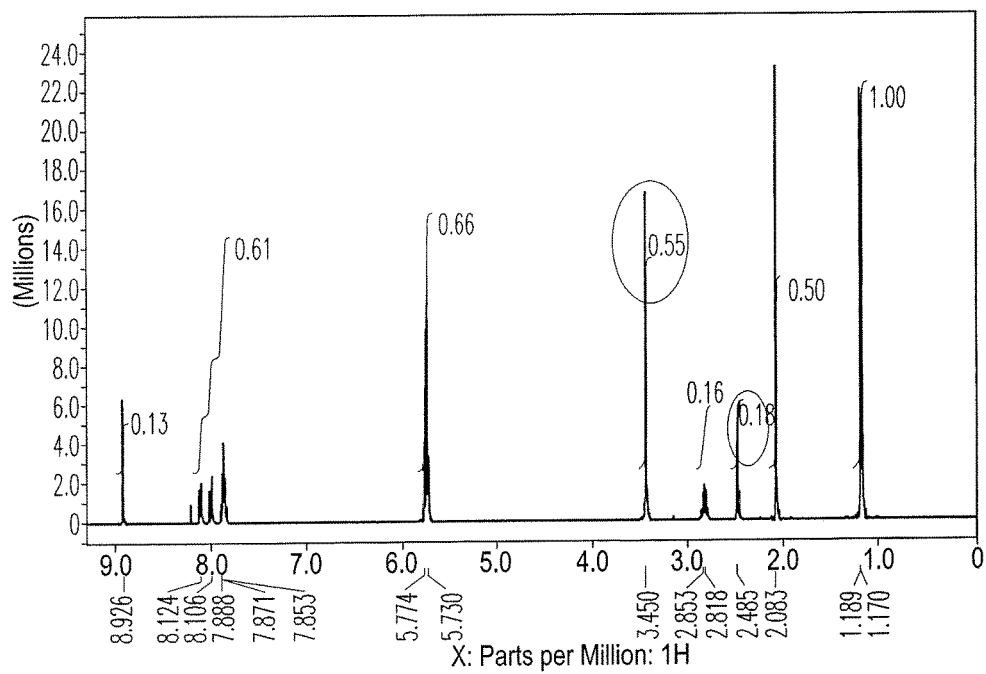
FIG. 3 is the 1H NMR spectrum of the anti-quorum and DNA cleaving agent of FIG. 1A.
Figure 4:
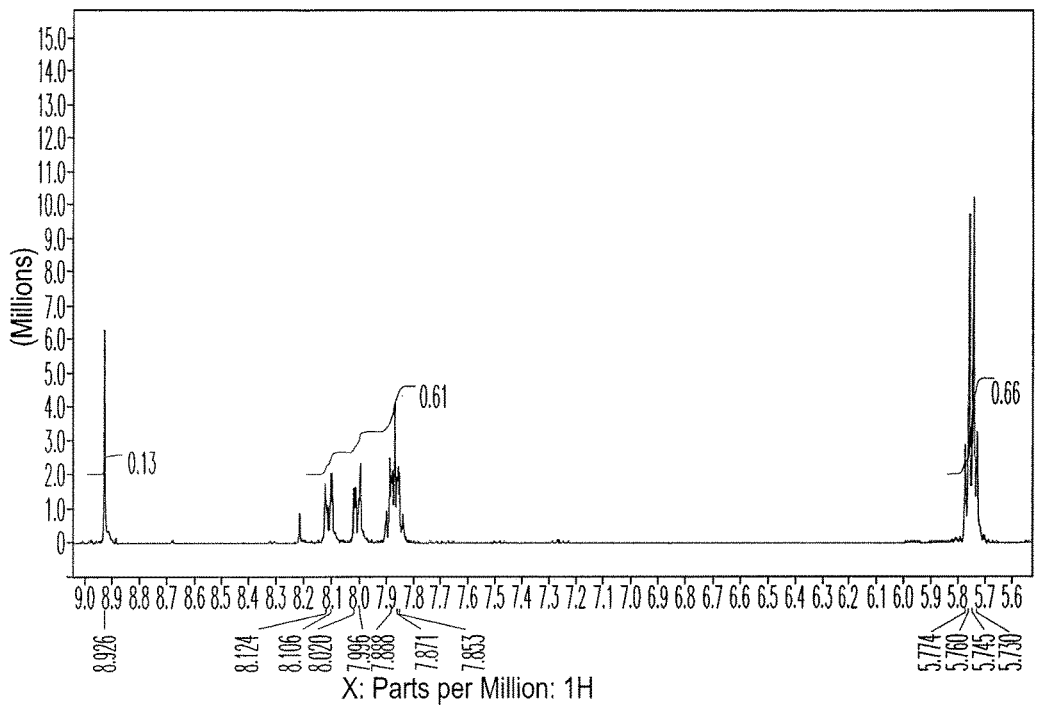
FIG. 4 is an expanded view of the 1H NMR spectrum of FIG. 3, showing the spectrum of the aromatic region of the anti-quorum and DNA cleaving agent of FIG. 1A in greater detail.
Figure 5:
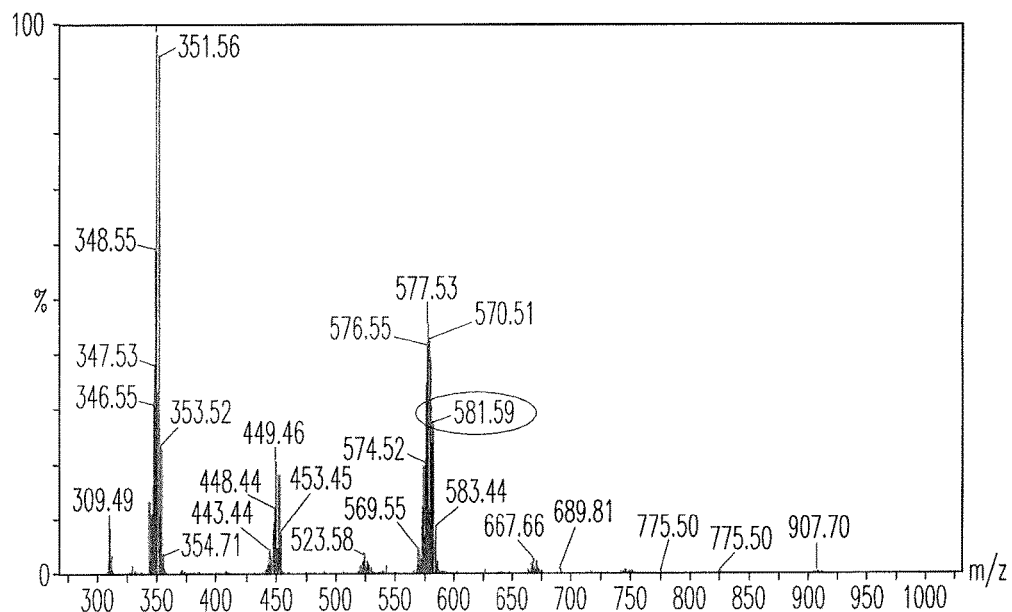
FIG. 5 is the ESI-MS (positive) spectrum of the anti-quorum and DNA cleaving agent of FIG. 1A.
Figure 6:
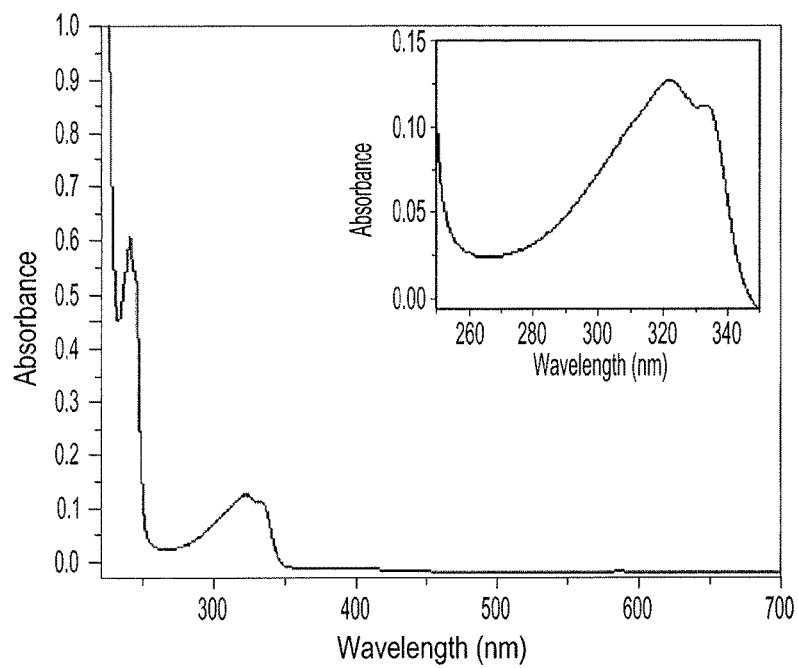
FIG. 6 is the UV-VIS spectrum of 10 µM of the anti-quorum and DNA cleaving agent of FIG. 1A in 10% DMSO, the inset showing a zoom of the spectrum in the range of 250-350 nm.
Figure 7:
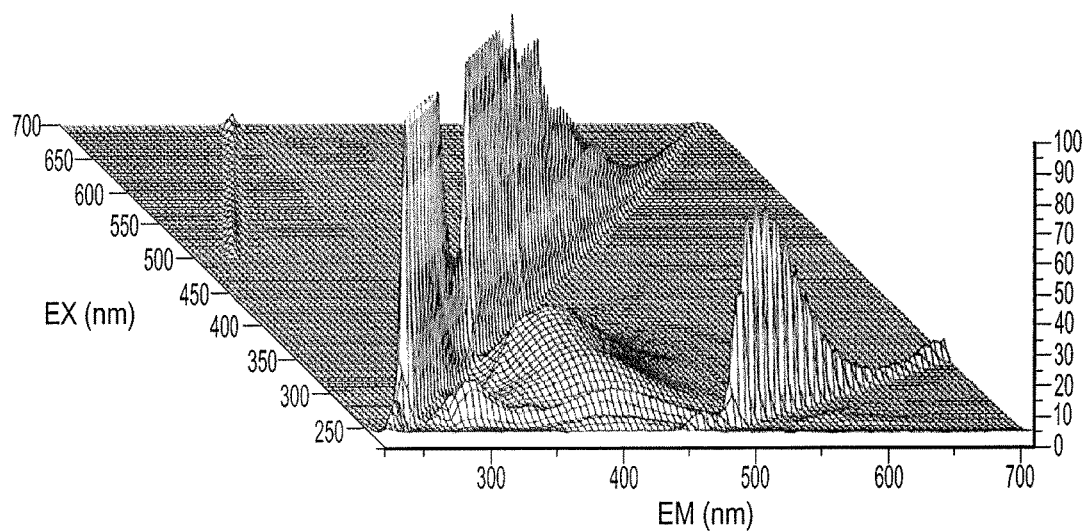
FIG. 7 is the 3-D fluorescent spectrum of the anti-quorum and DNA cleaving agent of FIG. 1A.
Figure 8:
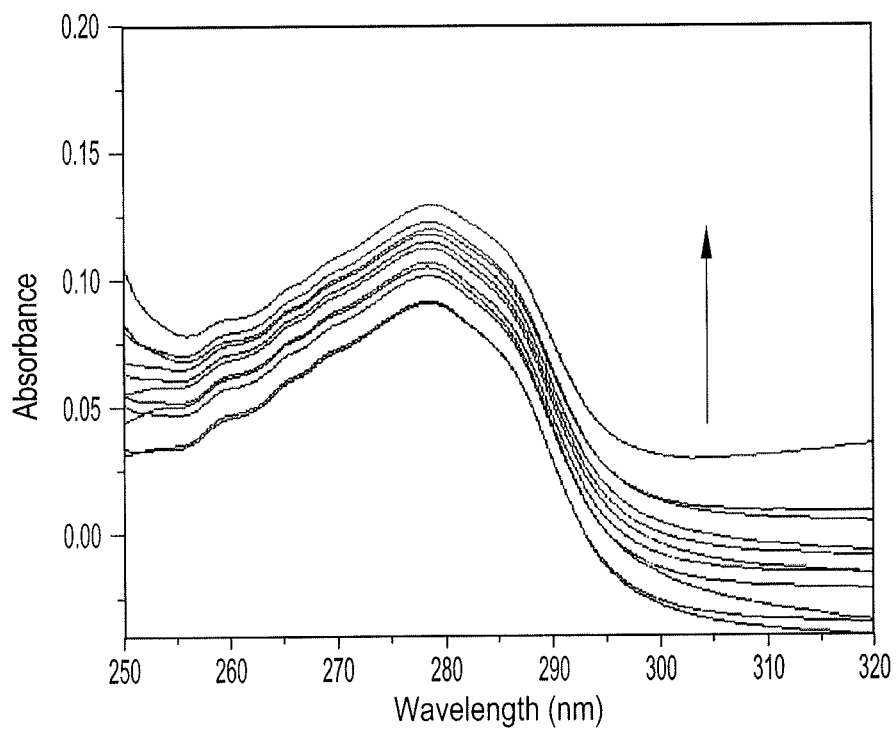
FIG. 8 is the difference UV absorption spectra of HSA (human serum albumin) in the presence of various amounts of the RAQA complex of FIG. 1A (obtained through the subtraction of Complex-1 spectrum of FIG. 6 from the spectra of complex-HSA conjugates containing the same amount of the complex), the concentration of HSA being 3 µM while the concentration of RAQA complex was varied from 0-50 µM in 5 µM increments between each run.
Figure 9A:
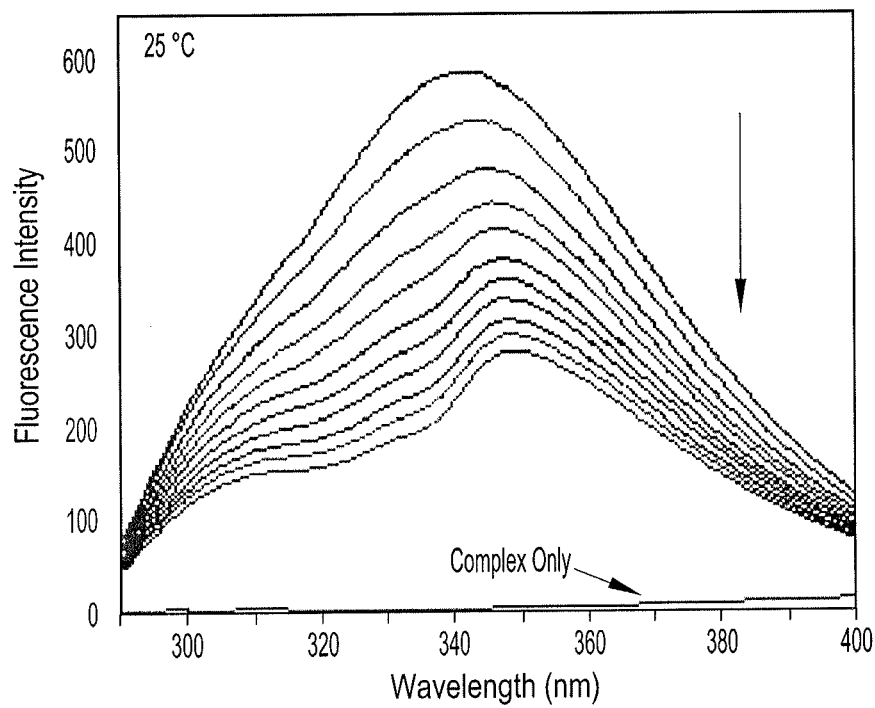
FIG. 9A is the fluorescence emission spectra ($\lambda_{ex}$=280 nm) of HSA at 25° C. in the presence of various amounts of the RAQA complex of FIG. 1A where the concentration of HSA is $3 \times 10^{-6}$ mol dm$^{-3}$, the concentration of the RAQA complex is varied from 0 to $50 \times 10^{-6}$ mol dm$^{-3}$ in $5 \times 10^{-6}$ mol dm$^{-3}$ increments, and the concentration of the pure complex is $100 \times 10^{-6}$ mol dm$^{-3}$.
Figure 9B:
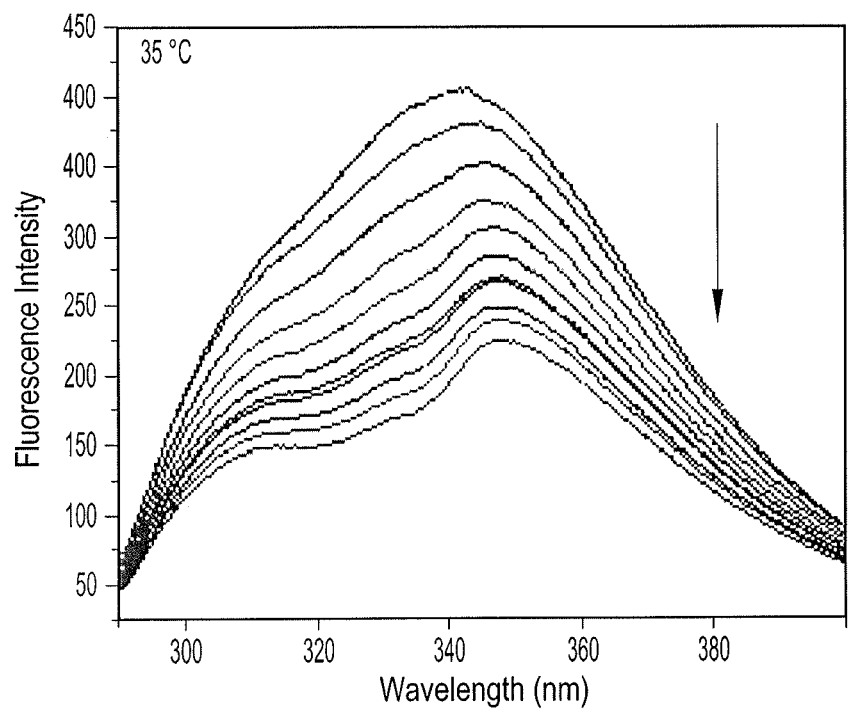
FIGS. 9B and 9C are the fluorescence emission spectra ($\lambda_{ex}$=280 nm) of HSA in the presence of various amounts of the RAQA complex of FIG. 1A where the concentration of HSA is $3 \times 10^{-6}$ mol dm$^{-3}$, the concentration of the RAQA complex is varied from 0 to $50 \times 10^{-6}$ mol dm$^{-3}$ in $5 \times 10^{6}$ mol dm$^{-3}$ increments at 35° C. and 45° C., respectively.
Figure 9C:
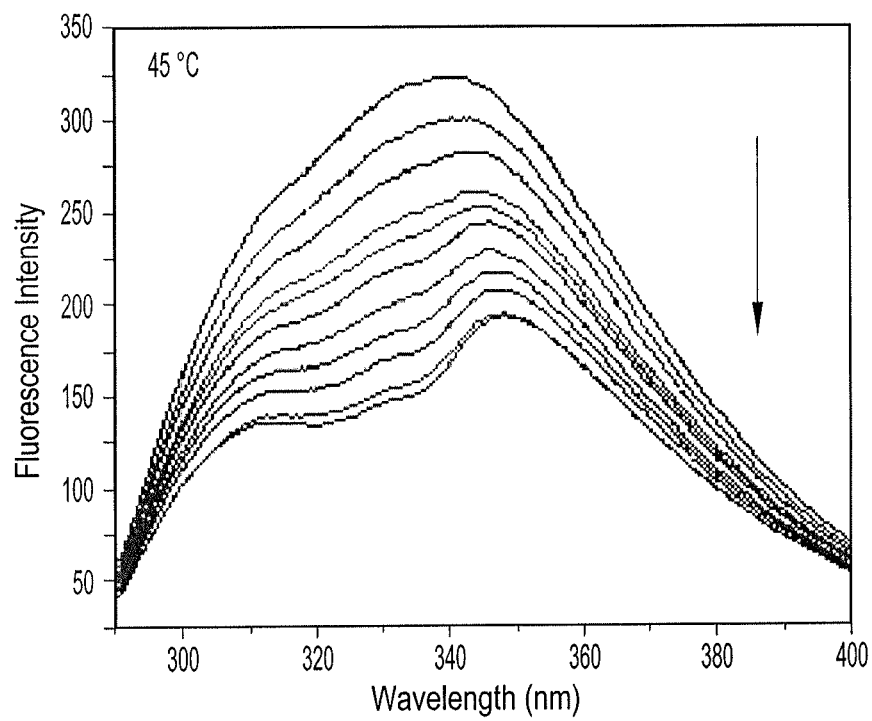
Figure 10A:
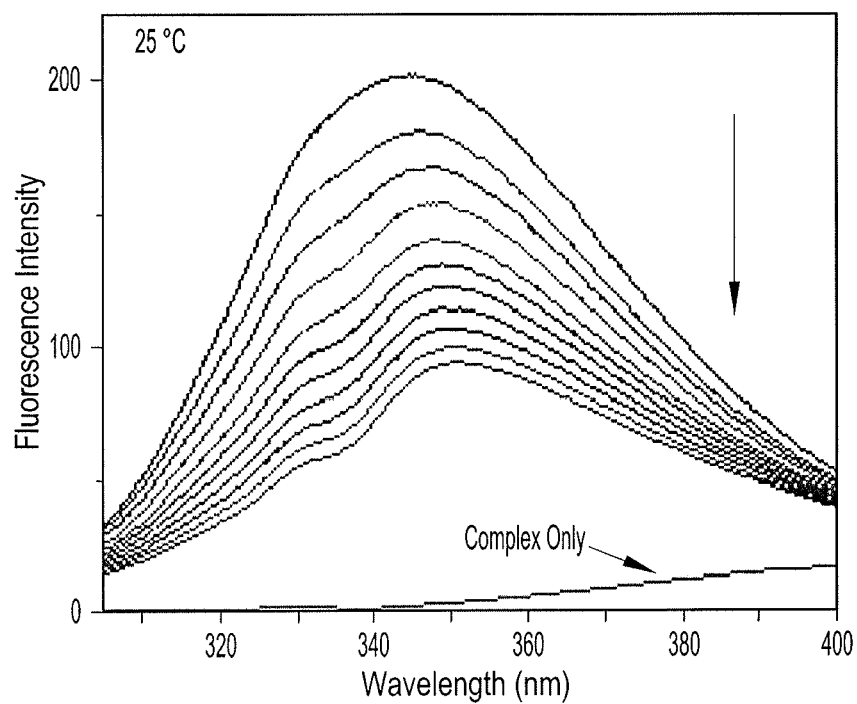
FIG. 10A is the fluorescence emission spectra ($\lambda_{ex}$=295 nm) of HSA at 25° C. in the presence of various amounts of the RAQA complex of FIG. 1A where the concentration of HSA is $3 \times 10^{-6}$ mol dm$^{-3}$, the concentration of the RAQA complex is varied from 0 to $50 \times 10^{-6}$ mol dm$^{-3}$ in $5 \times 10^{-6}$ mol dm$^{-3}$ increments, and the concentration of the pure complex is $100 \times 10^{-6}$ mol dm$^{-3}$.
Figure 10B:
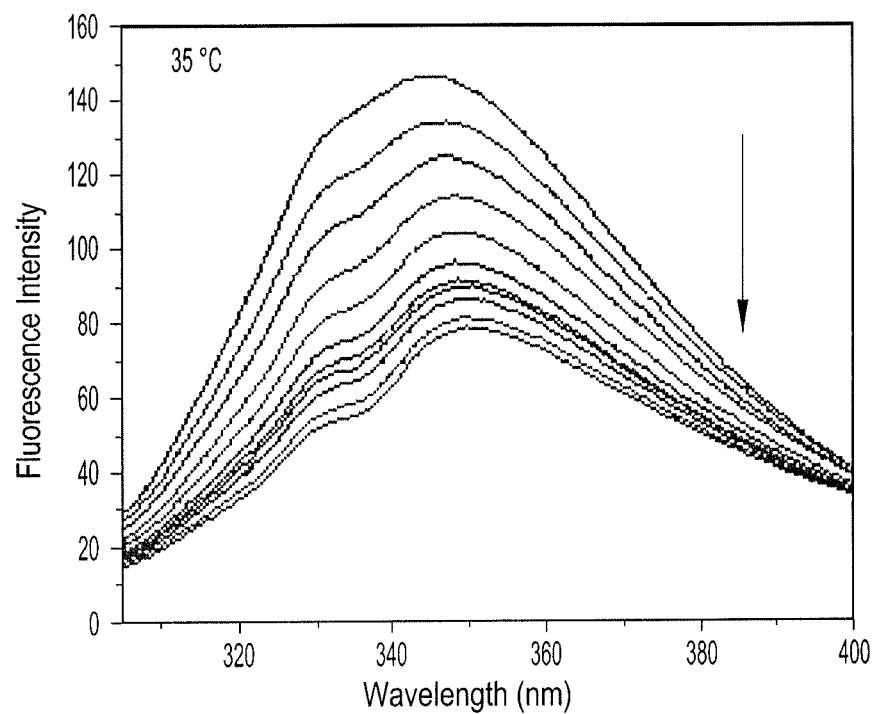
FIGS. 10B and 10C are the fluorescence emission spectra ($\lambda_{ex}$=295 nm) of HSA in the presence of various amounts of the RAQA complex of FIG. 1A where the concentration of HSA is $3 \times 10^{-6}$ mol dm$^{-3}$, the concentration of the RAQA complex is varied from 0 to $50 \times 10^{-6}$ mol dm$^{-3}$ in $5 \times 10^{-6}$ mol dm$^{-3}$ increments at 35° C. and 45° C., respectively.
Figure 10C:
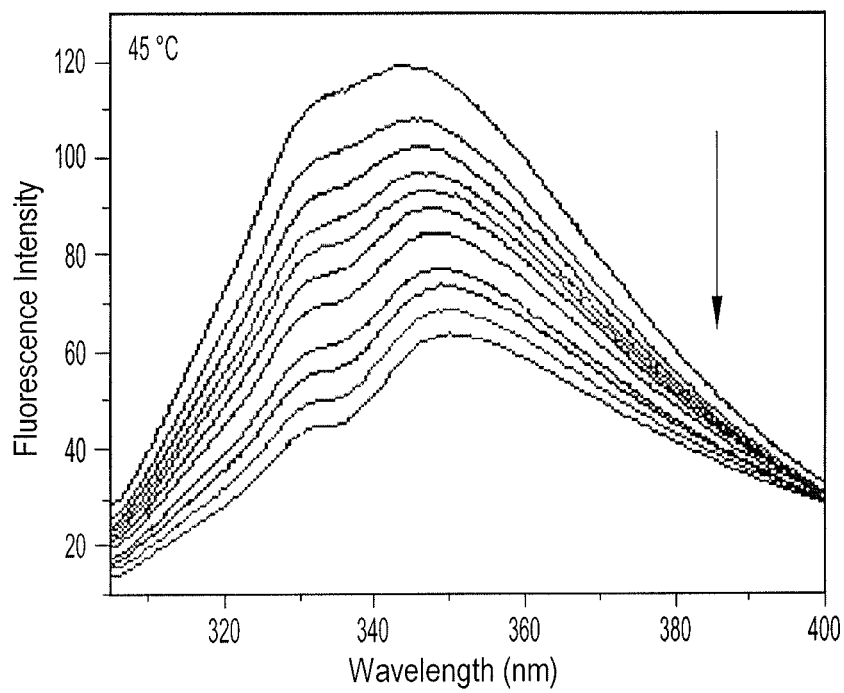
Figure 11A:
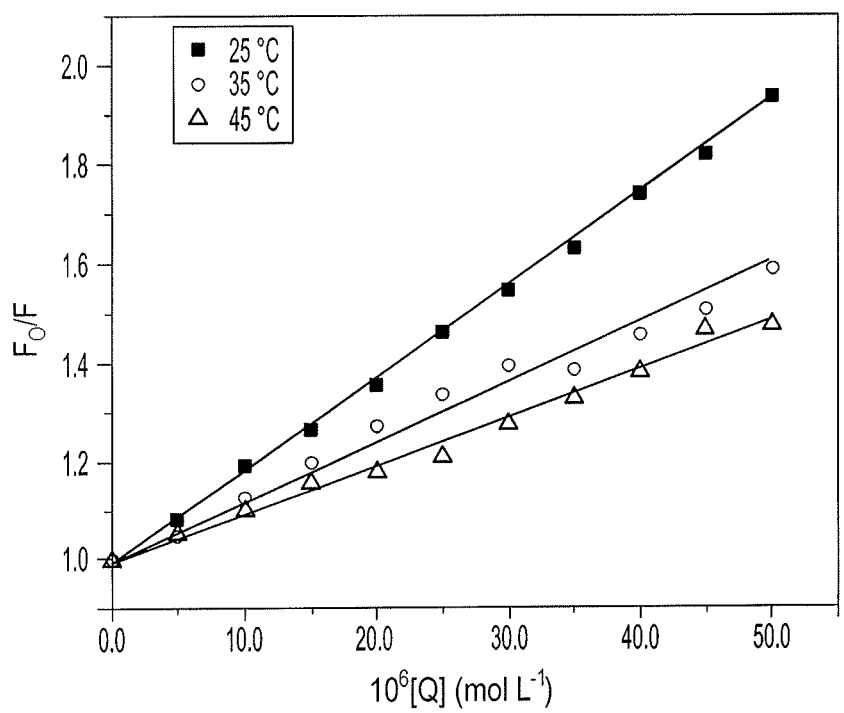
FIG. 11A is a plot of log (F0−F)/F as a function of log [RAQA complex of FIG. 1A] where [HSA]=$3 \times 10^{-6}$ mol dm$^{-3}$ and $\lambda_{ex}$=280 nm.
Figure 11B:
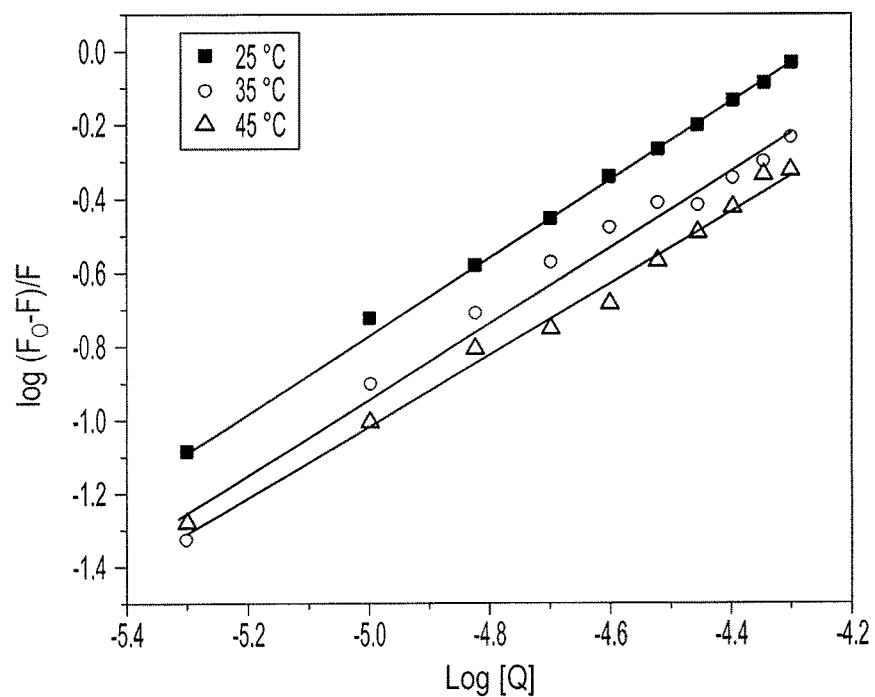
FIG. 11B is Stern-Volmer plots of HSA interaction with the RAQA complex of FIG. 1A at various temperatures where [HSA]=$3 \times 10^{-6}$ mol dm$^{-3}$ and $\lambda_{ex}$280 nm.
Figure 11C:
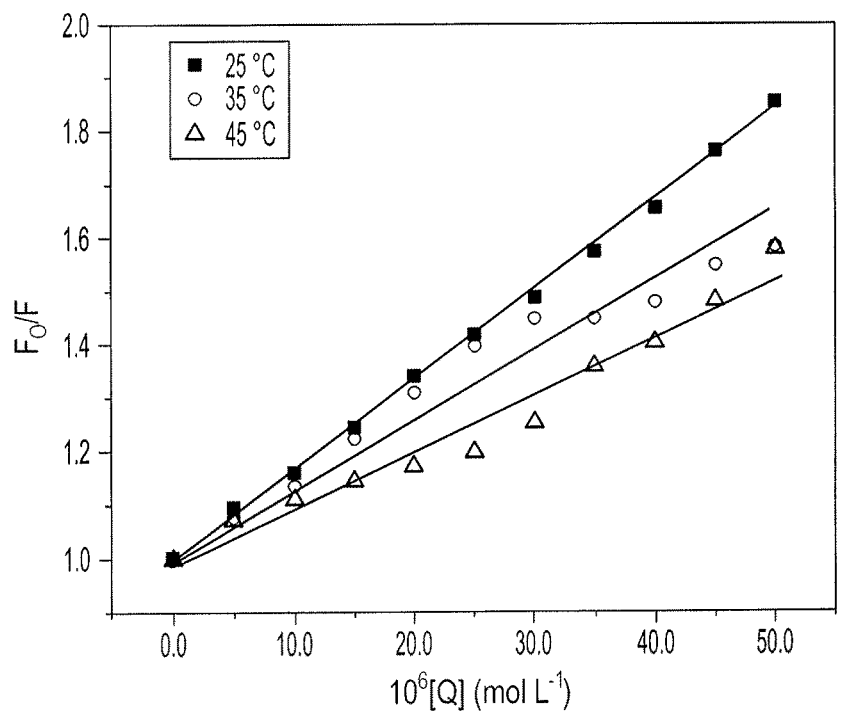
FIG. 11C is Stern-Volmer plots of HSA interaction with the RAQA complex of FIG. 1A at various temperatures where [HSA]=$3 \times 10^{-6}$ mol dm$^{-3}$ and $\lambda_{ex}$=295 nm.
Figure 11D:
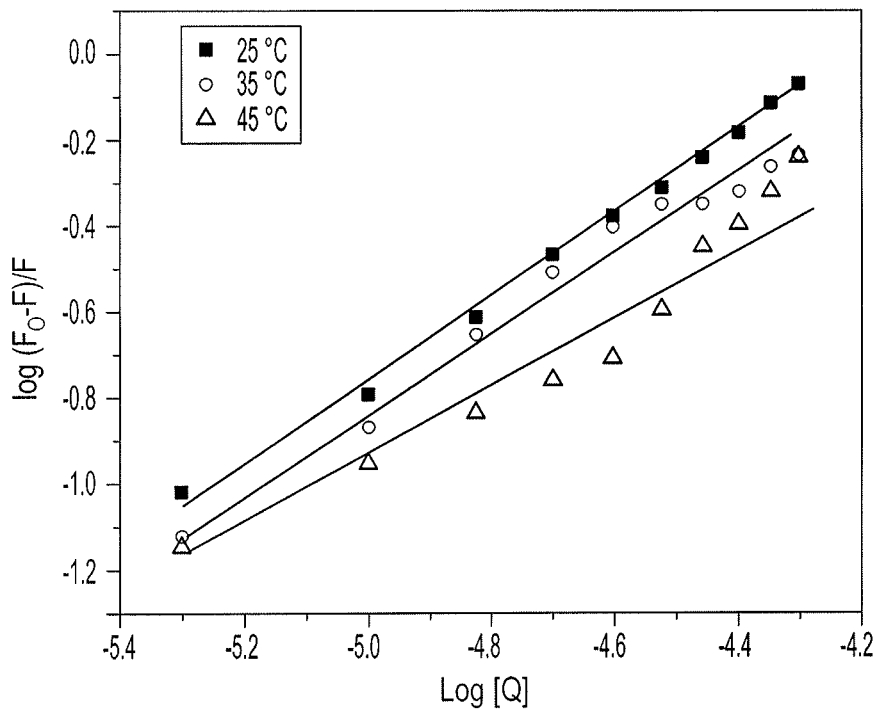
FIG. 11D is a plot of log (F0−F)/F as a function of log [the RAQA complex of FIG. 1A] where [HSA]=$3 \times 10^{-6}$ mol dm$^{-3}$ and $\lambda_{ex}$=295 nm.
Figure 23A:
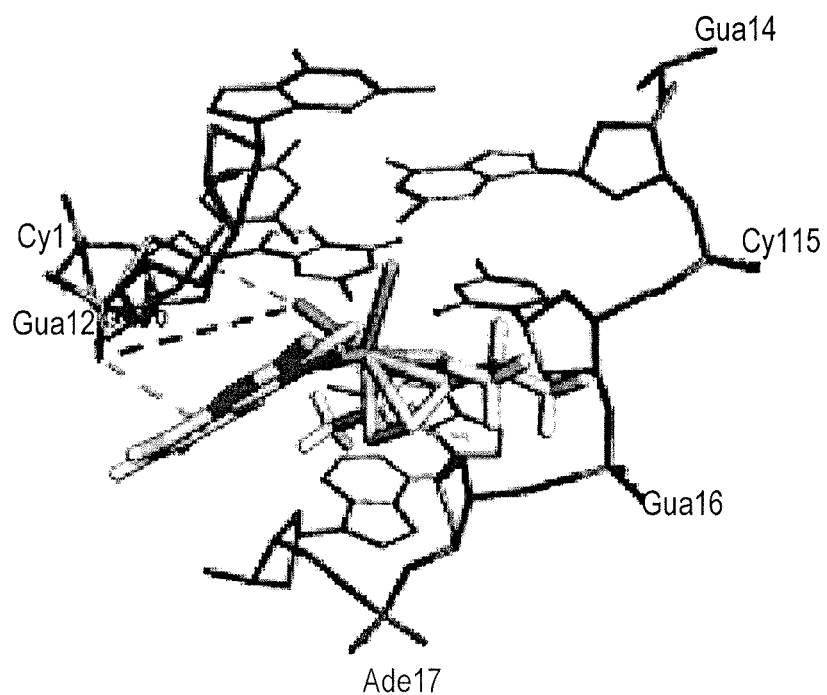
FIGS. 23A and 23B are molecular models showing docking of the RAQA complex of FIG. 1A on DNA and protein to confirm the side of binding in vitro and specific site recognition.
Figure 23B:
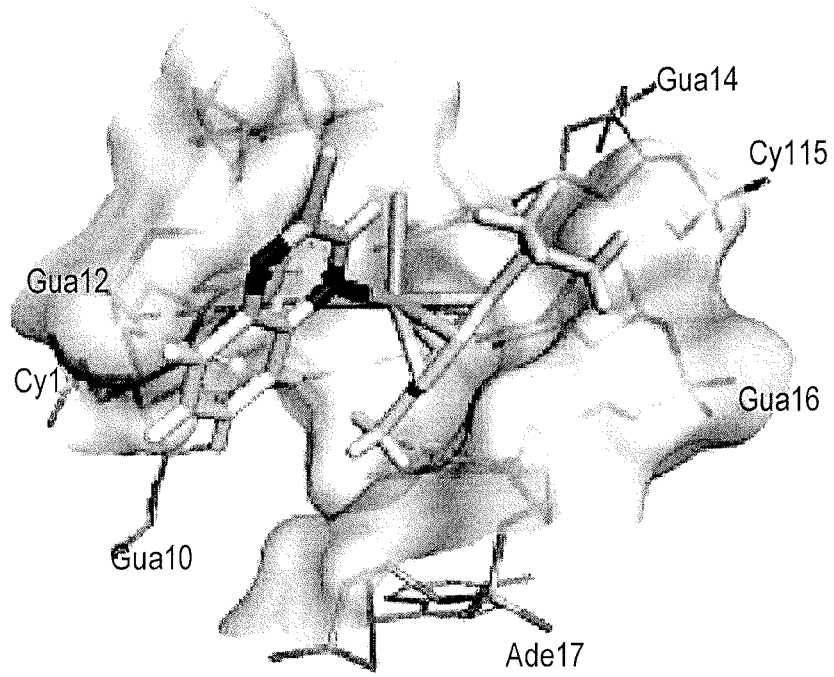

The structure of RAQA and ORTEP view are shown graphically in FIGS. 1A-1B, the dashed bonds in FIG. 1A between ruthenium and the ring of the cymene ligand reflecting the hapticity of ruthenium; the FT-IR spectrum is shown in FIG. 2; the $^1$H NMR spectra is shown in FIGS. 3-4; the ESI-MS spectrum is shown in FIG. 5; the UV spectrum is shown in FIG. 6; and the 3-D fluorescent spectrum is shown in FIG. 7. Spectroscopic (FIGS. 8-18) and docking studies (FIG. 23A-B) were used to further validate the mode of binding to DNA.

At the Cambridge Crystallographic Data Centre, the data for the structure shown in FIG. 1A have been assigned to deposition number CCDC 1519421. The compound name is RAQA (Ruthenium Anti-Quorum Agent); the formula is C18 H19 C13 N2 Ru1; and the unit cell parameters are a 9.8549(4) b 13.9508(6) c 7.0500(3) Pc.

The method for preparation of the p-cymene Ru(II) based complex of Formula (I). comprises the steps of (a) dissolving chloroquinoxaline in a solvent system to obtain a solution of ligands; and (b) complexing the ligand solution with an alcoholic solution of p-cymene ruthenium under stirring at a temperature ranging between 75-80° C. for a time period ranging between 6-8 hours to obtain a uniformly dispersed ruthenium-based complex of Formula (I). The p-cymene ruthenium complex obtained in step (b) is filtered and the solvent is left to evaporate slowly to afford a crystalline p-cymene ruthenium complex. The resultant crystals may then be re-crystallized with methanol and dichloromethane and dried under vacuum. The p-cymene ruthenium complex of FIG. 1A can be present as a complex, in particular a pharmaceutically acceptable potential anti-quorum drug or a pharmaceutically acceptable salt thereof.

Furthermore, the p-cymene ruthenium complex of FIG. 1A has been characterized by elemental analysis, FTIR, NMR, ESI-MS and single X-ray crystallography. By the present disclosure, the p-cymene Ruthenium complex of FIG. 1A is isolated in its crystalline form.

Further, with regarding to the p-cymene ruthenium complex of FIG. 1A intercalation of DNA helix, this intercalative binding is due to the overlap of a planar aromatic moiety with the stacking base pairs of DNA. More specifically, the cleavage proceeds by a hydrolytic mechanism in aqueous solution, as Ru—Cl bonds are labile and Cl-anions exchange easily with water molecules. This allows the DNA to be cleaved readily at base pairs that include guanine, such as at the $N_7$ of each guanine.

The present disclosure is further described in light of the following examples which are set forth for illustration purpose only and not to be construed as limiting the scope of the disclosure.

In the following examples, 2-chloroquinoxaline, DMSO, Human Serum Albumin (HSA), Dichloro($\eta^6$-p-cymene) ruthenium dichloride dimer, solvents, Phosphate buffer, HCl, and NaCl were obtained from Sigma-Aldrich.

*C. violaceum* CV12472 and *P. aeruginosa* PAO1 (C4 and 3-oxo-C12 HSL producer) are the bacterial strains used. Luria-Bertani (LB) medium was used to grow bacterial strains at 30° C. for 24 hours.

MICs of the RAQA complex were determined against *C. violaceum* CV12472 and *P. aeruginosa* PAO1 by the broth macrodilution method (CLSI, 2007). For the assessment of anti-virulence and anti-biofilm activity, Sub-MICs were selected in the above test strains.

The extent of violacein production by Chromobacterium *violaceum* (CV12472) in the presence of Sub-MICs of the test agent was studied by extracting violacein and spectrophotometric quantification using the Blosser and Gray method with little modification. One-ml culture from each flask was centrifuged at 13000 rev/min for 10 minutes to precipitate the insoluble violacein. The culture supernatant was discarded, and 1 ml of DMSO was added to the pellet. The solution was vortexed vigorously for 30 seconds to completely solubilize violacein and centrifuged at 13000 rev/min for 10 minutes to remove the cells. Two hundred microliters of the violacein-containing supernatants were added to 96-well flat bottomed microplates (Polylab, India), at four wells per each solution, and the absorbance was read with a microplate reader (Thermo Scientific Multiskan Ex) at a wavelength of 585 nm. Reduction in the production of pigment in the presence of test agents was measured in terms of % inhibition as, [(OD of control−OD of treated)/OD of control]×100.

The effect of Sub-MICs of test agents on virulence factors of *P. aeruginosa*, such as LasB elastase, pyocyanin, swarming motility, EPS extraction and quantification, was assessed as described previously. The effect of the synthesized complex on biofilm formation was measured using the microtiter plate assay. Briefly, 1% overnight cultures (0.4 OD at 600 nm) of test pathogens were added into 1 mL of fresh LB medium in the presence and in the absence of sub-MICs of test agents. Bacteria were allowed to adhere and grow without agitation for 24 hours at 30° C. After incubation, the microtitre plate was emptied by removing the media along with free-floating planktonic cells, and the wells were gently rinsed twice with sterile water. The surface-attached cells (biofilm) were stained with 200 µL of 0.1% crystal violet (CV) (Hi-media, Mumbai, India) solution. After 15 minutes, CV solution was discarded completely and wells were filled with 200 µL of 95% ethanol to solubilize CV from the stained cells. The biofilm biomass was then quantified by measuring the absorbance at OD 470 nm in a microplate reader (Thermo Scientific Multiskan Ex, India).

All experiments were performed in triplicate, and the data obtained from experiments were presented as mean values. The difference between control and test were analyzed using student's t test.

Infrared spectra were recorded as solid KBr pellets, using a Shimadzu IRAffinity-1 spectrometer with a resolution of 4 $cm^{-1}$. Elemental analysis (C, H, N) were performed on a PerkinElmer 2400 Series II CHNS/O system. NMR spectra were recorded using a JEOL-ECP-400 spectrometer. Positive electrospray mass spectra were obtained with a Series 1100 MSI detector HP spectrometer, using MeOH as the mobile phase. Solutions for electrospray ionization mass spectrometry (ESI-MS) were prepared using reagent-grade methanol, and the obtained data (masses and intensities) were compared with those calculated by using the IsoPro isotopic abundance simulator, version 2.1.

The molecular docking studies have been performed by using Hex 8.0.0. All rotatable bonds within the ligand were allowed to rotate freely, and receptor was considered rigid. The crystal structure of the B-DNA dodecamer d(CGC-GAATTCGCG)$_2$ (SEQ ID NO. 1)(PDB ID: 1BNA), human-DNA-Topo-I (PDB ID: 1SC7) and human Topo-IIα (PDB ID: 1ZXM) were retrieved from the protein data bank (http://www.rcsb.org./pdb). Visualization of minimum energy favorable docked poses has been performed using Discovery Studio 4.1 and PyMol. DNA binding experiments that included spectral absorption studies, and fluorescence conformed to the standard methods and practices previously adopted by our laboratory. Standard error limits were estimated using all data points. Circular dichroic spectra of DNA were obtained by using Circular Dichroism (CD) Spectrometer. All experiments were done using a 200 µL quartz cell. Each CD spectrum was collected after averaging over at least 3 accumulations using a scan speed of 100 nm $min^{-1}$ and a 5 s response time. Machine plus cuvette baselines were subtracted, and the resultant spectra zeroed outside the absorption bands.

Single crystal X-ray data of complex 1 (RAQA) was collected at 100 K on a Bruker SMART APEX CCD diffractometer using graphite monochromatic MoK$_\alpha$ radiation ($\lambda$=0.71073 Å). The linear absorption coefficients, scattering factors for the atoms, and the anomalous dispersion corrections were referred from the International Tables for X-ray Crystallography. The data integration and reduction were worked out with SAINT software. Empirical absorption correction was applied to the collected reflections with SADABS program, and the space group was determined using XPREP. The structure was solved by direct methods using SHELXTL and refined on $F^2$ by full-matrix least-squares using the SHELXTL programme package. Only a few H atoms could be located in the difference Fourier maps in the structure. The rest were placed at calculated positions using idealized geometries (riding model) and assigned fixed isotropic displacement parameters. All non-H atoms were refined anisotropically. Several DFIX commands were used for fixing some bond distances in complex 1 (RAQA).

Example 1

Synthesis of RAQA

The active 2-chloroquinoxaline was added to a solution of [{Ru(η$^6$-p-cymene)Cl$_2$}$_2$] in dry alcohol (methanol, ethanol, propanol) in different molar ratios and the mixture was allowed to reflux and stirred for about 2-6 hours. Then, the reaction mixture was separated and cooled to room temperature and left for slow evaporation. The characteristic colored single crystals were obtained after a few days in the mother liquor at appropriate temperature. The structure and purity were confirmed by elemental analysis, FT-IR (FIG. 2), ESI-MS (FIG. 5), $^1$HNMR spectroscopy (FIGS. 3-4), and single X-ray crystallography. M.p. 190° C., Yield: 78%. Anal. Calcd for $C_{18}H_{19}Cl_3N_2Ru.2H_2O$: C, 42.43; H, 3.79; N, 5.52%. Found: C, 43.00; H, 3.81; N, 5.57%. FT-IR ($cm^{-1}$): 3446 ν(O—H), 3070 ν(C—H), 1636, 1566, 1531, 1490, 1398 ν(C=N) and ν(C=C), 1155, 1107, 860, 761 ν(aromatic). $^1$H NMR (400 MHz, CD$_3$SOCD$_3$, d$_6$): 8.92 (s, 1H, CH ligand), 8.12-8.09 (dd, 1H, $J^{H-H}$=8.0 Hz, CH Ligand), 8.02-7.99 (dd, 1H, $J^{H-H}$=7.2 Hz, CH ligand), 7.88-7.85 (m, 21, CH ligand), 5.77-5.73 (m, 4H, p-cymene), 2.85-2.81 (m, 1H, CH(CH$_3$)$_2$ of p-cymene), 2.08 (s, 3H, CH$_3$— of p-cymene), 1.18 (s, 6H, CH(CH$_3$)$_2$ of p-cymene). ESI-MS (+ve, CD$_3$SOCD$_3$ {DMSO}): m/z=581.59 (obs.) {580.92 (expected)} for [C$_{18}$H$_{19}$Cl$_3$N$_2$Ru+DMSO+2H$_2$O] presence of DMSO and H$_2$O is quite evident from FT-IR and $^1$H NMR spectra.

Example 2

Interaction of RAQA with HSA Protein

Absorption spectroscopy is an important and basic tool for understanding the ligand-protein interaction. Several amino acids, such as tyrosine, phenylalanine, and tryptophan, display the peak behavior at 278 nm, and any change in the peak intensity or wavelength of maximum absorption ($\lambda_{max}$) may be ascribed to the change in the structure of protein due to the interaction. Therefore, the interaction of the RAQA complex and HSA (human serum albumin) was studied using absorption spectroscopy, and the difference spectra are given in FIG. 8. It is evident from FIG. 8 that the absorption intensity of HSA increases while the wavelength of absorption maximum remains unchanged on increasing the concentration of RAQA complex. This may be attributed to the formation of ground state complex between HSA and the RAQA complex.

HSA possesses one tryptophan residue (Trp-214) and several tyrosine residues distributed along the protein domain, which are responsible for the intrinsic fluorescence of the protein. Any change in the microenvironment may alter the intrinsic fluorescence properties of HSA. When excited at 280 nm, the fluorescence reflects the emission of both the tryptophan and tyrosine residues, whereas excitation at 295 nm diminishes the involvement of tyrosine. The fluorescence quenching spectra of HSA in the presence of an increasing quantity of RAQA complex are given in FIGS. 9A-9C and FIGS. 10A-10C. Excitation at both wavelengths gives a similar type of spectra, with the wavelength of emission maximum at around 340 nm, although the intensity in the case of $\lambda_{ex}$=280 nm is higher due to the involvement of tyrosine emission. As described above, the RAQA complex is also fluorescent, but the intensity is almost negligible as compared to the fluorescence of HSA. Successive addition of RAQA complex to the HSA results in the progressive quenching of the fluorescence of HSA with a prominent red shift that may be attributed to the dominance of electrostatic forces in the interaction between metal complex and protein.

Due to the absorption of the complex at the excitation wavelength, inner filter effect was corrected for the fluorescence measurements by using the following equation:

$$F_{corr}=F_{obs} \times e^{(A_{exi}+A_{emi})/2}, \quad (1)$$

where $F_{corr}$ and $F_{obs}$ are abbreviations for fluorescence emission intensities, corrected and observed, respectively, and $A_{exi}$ and $A_{emi}$ are the absorbance at the excitation and emission wavelengths, respectively. The data obtained from corrected emission spectra were used for further analysis.

The Stern-Volmer equation was used to obtain the quenching parameters, which is given as:

$$\frac{F_o}{F} = K_{sv}[Q] + 1, \quad (2)$$

where $F_o$ and $F$ are the fluorescence intensities in absence of and in presence of quencher (complex). Further, $K_{sv}$ is the Stern-Volmer quenching constant, which is defined as:

$$K_{sv}=k_q\tau_0 \quad (3)$$

where $k_q$ is the bimolecular rate constant of the quenching reaction and $\tau_0$ is the average integral fluorescence life time of Trp, which is ~5.7×10$^{-9}$ sec. To determine the binding constant ($K_b$) and a number of binding sites (n), the Stern-Volmer equation can be modified as:

$$\log\left(\frac{F_o}{F} - 1\right) = \log K_b + n\log[Q]. \quad (4)$$

From the observed effect of temperature on the Stern-Volmer quenching constant (inversely proportional), it can be concluded that the quenching is static and there is approximately 1:1 binding between HSA and the RAQA complex (FIGS. 11A-11D).

Figure 12A:
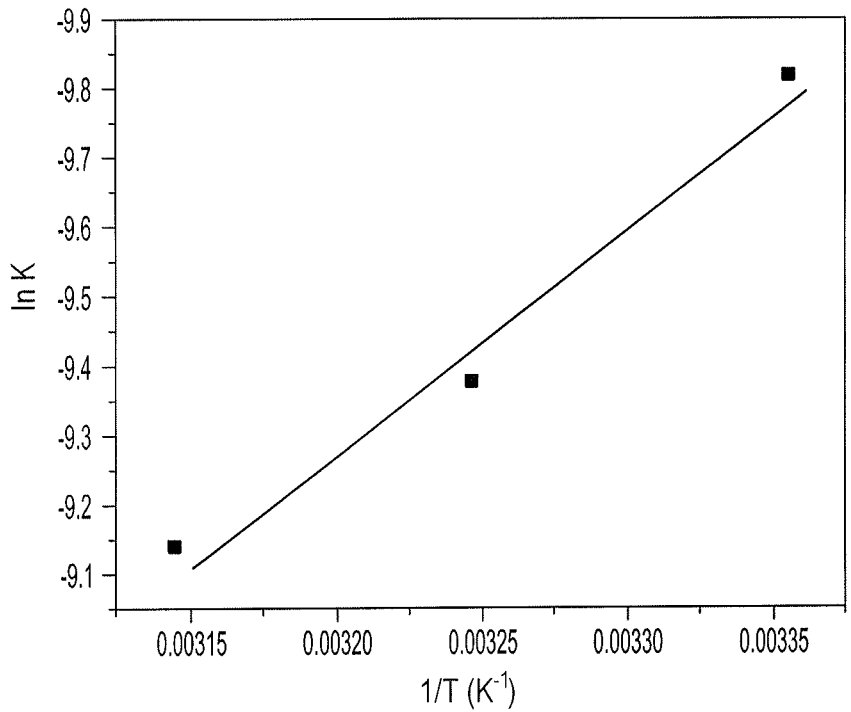
FIGS. 12A and 12B are Van't Hoff plots of HSA interaction with the RAQA complex of FIG. 1A where [HSA]=$3 \times 10^{-6}$ mol dm$^{-3}$ and $\lambda_{ex}$=280 nm and 295 nm, respectively.
Figure 12B:
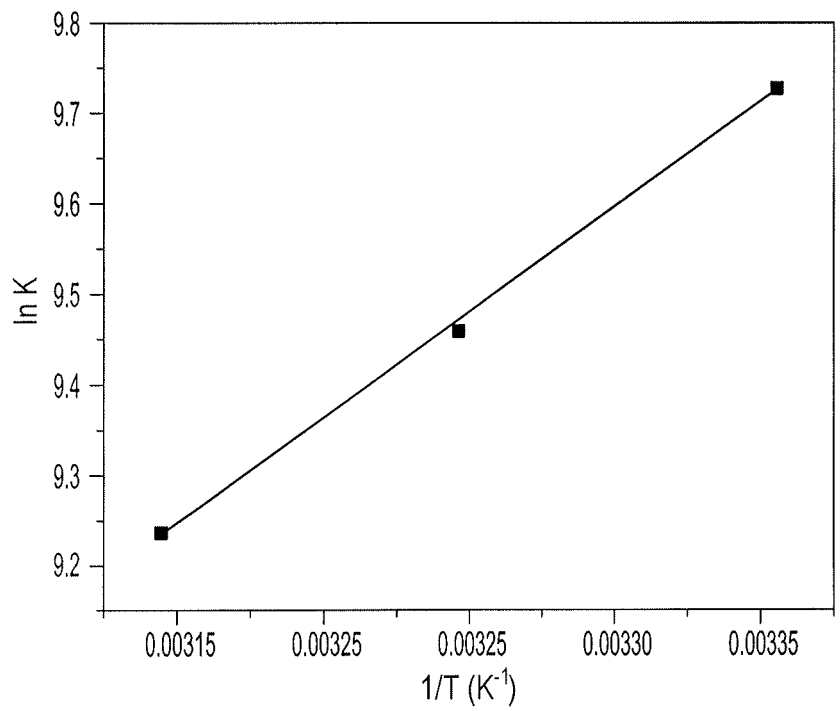
Figure 13:
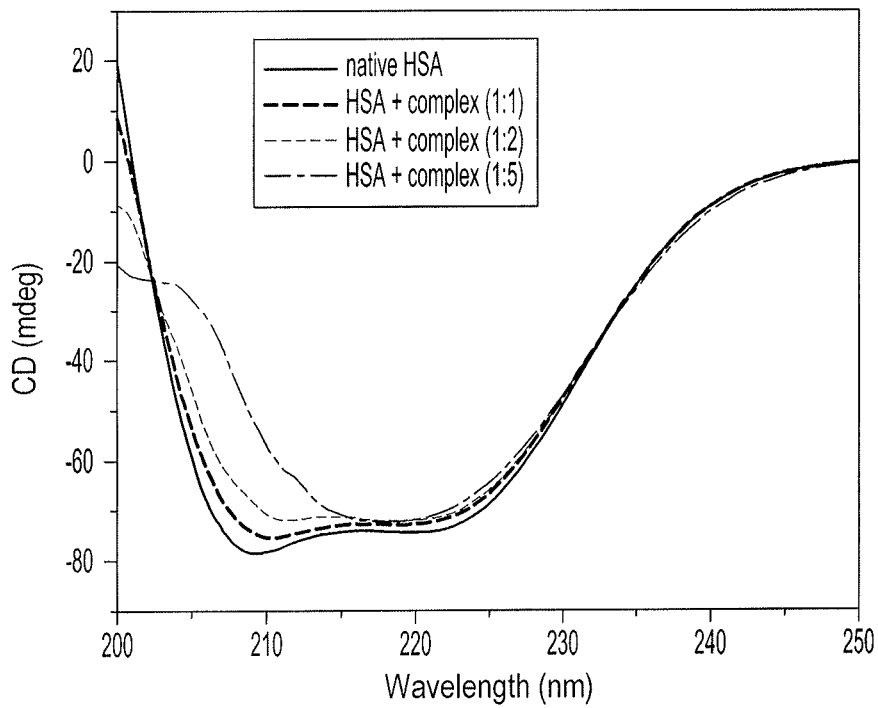
FIG. 13 is the Far-UV CD spectra of HSA in the presence of the RAQA complex of FIG. 1A at 25° C. and pH 7.4 where [HSA]=$3.0 \times 10^{-6}$ mol dm$^{-3}$ and [complex]=0, $3.0 \times 10^{-6}$, $6.0 \times 10^{-6}$, and $15.0 \times 10^{-6}$ mol dm$^{-3}$, respectively.

The thermodynamic parameters, enthalpy change ($\Delta H$), and entropy change ($\Delta S$) between HSA and RAQA complex were calculated using a Van't Hoff plot. If the $\Delta H$ does not change too much on the temperature variation, both $\Delta H$ and $\Delta S$ can be evaluated from the Van't Hoff equation:

$$\ln K = \frac{-\Delta H}{RT} + \frac{\Delta S}{R}, \quad (5)$$

where K is the association or binding constant at temperature T and R is the gas constant. Van't Hoff plots are shown in FIGS. 12A-12B. After calculating the $\Delta H$ and $\Delta S$ from the linear regression of the plots of ln K vs. 1/T, the free energy change ($\Delta G$) can be calculated as:

$$\Delta G = \Delta H - T\Delta S. \quad (6)$$

TABLE 1

Stern-Volmer quenching constants and parameters for interaction of HSA with RAQA, $\lambda_{ex}$ = 280

| T | Stern-Volmer quenching constants | | | Binding parameters | | | Thermodynamic Parameters | | |
|---|---|---|---|---|---|---|---|---|---|
| (K) | $K_{SV}$ (M$^{-1}$) | $K_q$ (M$^{-1}$s$^{-1}$) | $R^2$ | n | K (M$^{-1}$) | $R^2$ | $\Delta G$ (KJ mol$^{-1}$) | $\Delta H$ (KJ mol$^{-1}$) | $\Delta S$ (J mol$^{-1}$ K$^{-1}$) |
| 298 | 1.83 × 10$^4$ | 3.21 × 10$^{12}$ | 0.9990 | 1.0 | 2.51 × 10$^4$ | 0.9983 | −24.24 | −26.68 | −8.16 |
| 308 | 1.18 × 10$^4$ | 2.07 × 10$^{12}$ | 0.9825 | 1.0 | 1.74 × 10$^4$ | 0.9798 | −24.16 | | |
| 318 | 0.95 × 10$^4$ | 1.67 × 10$^{12}$ | 0.9884 | 0.96 | 60 × 10$^4$ | 0.9896 | −24.09 | | |

TABLE 2

Stern-Volmer quenching constants and parameters for interaction of HSA with RAQA, $\lambda_{ex}$ = 295

| T | Stern-Volmer quenching constants | | | Binding parameters | | | Thermodynamic Parameters | | |
|---|---|---|---|---|---|---|---|---|---|
| (K) | $K_{sv}$ (M$^{-1}$) | $K_q$ (M$^{-1}$ s$^{-1}$) | $R^2$ | n | K (M$^{-1}$) | $R^2$ | $\Delta G$ (KJ mol$^{-1}$) | $\Delta H$ (KJ mol$^{-1}$) | $\Delta S$ (J mol$^{-1}$ K$^{-1}$) |
| 298 | 1.67 × 10$^4$ | 2.93 × 10$^{12}$ | 0.9985 | 0.96 | 1.18 × 10$^4$ | 0.9963 | −24.08 | −19.37 | 16.00 |
| 308 | 1.28 × 10$^4$ | 2.25 × 10$^{12}$ | 0.9513 | 0.91 | 0.49 × 10$^4$ | 0.9807 | −24.24 | | |
| 318 | 1.02 × 10$^4$ | 1.80 × 10$^{12}$ | 0.9884 | 0.89 | 0.32 × 10$^3$ | 0.9464 | −24.40 | | |

HSA is an α-helical protein with around 67% of α-helical content. Successive addition of RAQA complex causes the protein to change its conformation from α-helix to β-sheets.

Figure 14A:
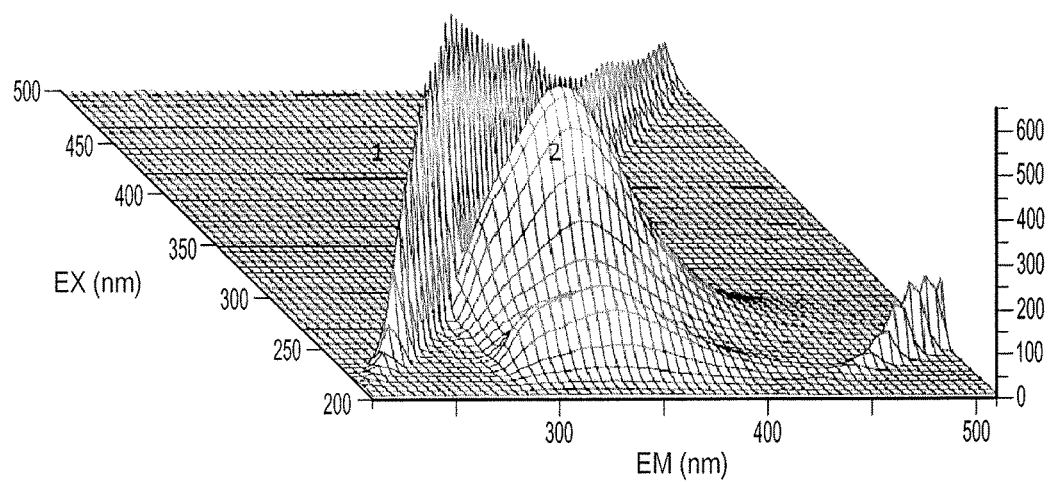
FIGS. 14A and 14B are 3-D fluorescence spectra of HSA ($3.0 \times 10^{-6}$ mol dm$^{-3}$) in the absence of the RAQA complex of FIG. 1A and in the presence of $50 \times 10^{-6}$ mol dm$^{-3}$ of the RAQA complex of FIG. 1A, respectively.
Figure 14B:
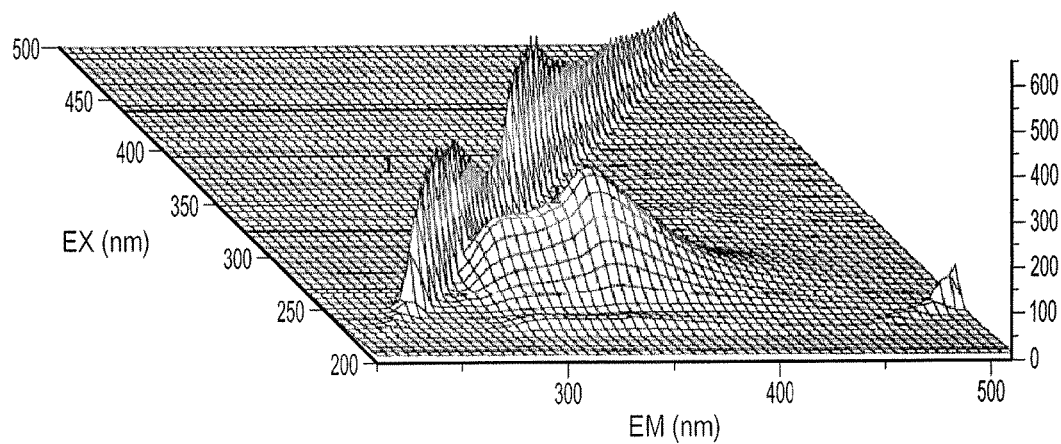
Figure 15:
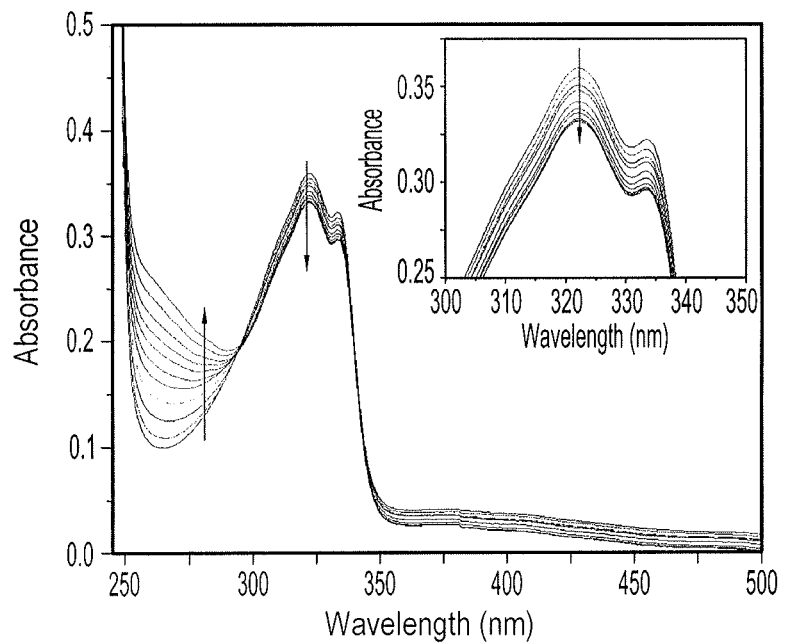
FIG. 15 is UV-VIS absorption spectra of the RAQA complex of FIG. 1A ($50.0 \times 10^{-6}$ mol dm$^{-3}$) in the presence of increasing concentrations of CT-DNA (calf thymus DNA) ($0-50.0 \times 10^{-6}$ mol dm$^{-3}$).
Figure 16:
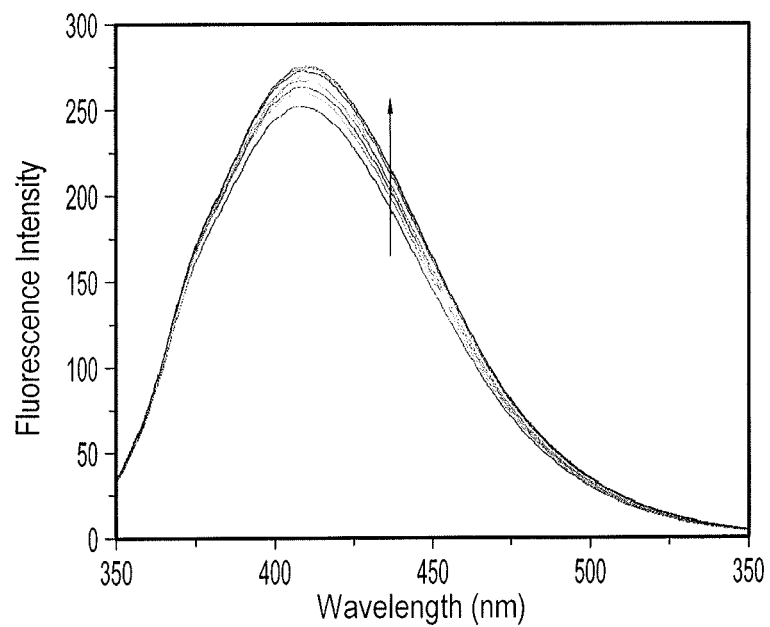
FIG. 16 is fluorescence emission spectra of the RAQA complex of FIG. 1A ($50.0 \times 10^{-6}$ mol dm$^{-3}$) in the presence of increasing concentrations of CT-DNA.

Referring to FIGS. 14A and 14B, peak 1 is the Rayleigh scattering peak that arises due to excitation and emission at the same wavelength, and at 350 nm, it signifies the relative size of the protein. It is clear from FIGS. 14A-14B that there is not much change in the intensity of peak 1 at 350 nm. Peak 2 is an emission peak that arises due to the excitation of tryptophan and tyrosine residues and reflects the microenvironment of these residues. The decrease in the intensity of peak 2 is due to the quenching of fluorophores by the RAQA complex.

Example 3

Interaction Between RAQA Complex and CT-DNA

Figure 17A:
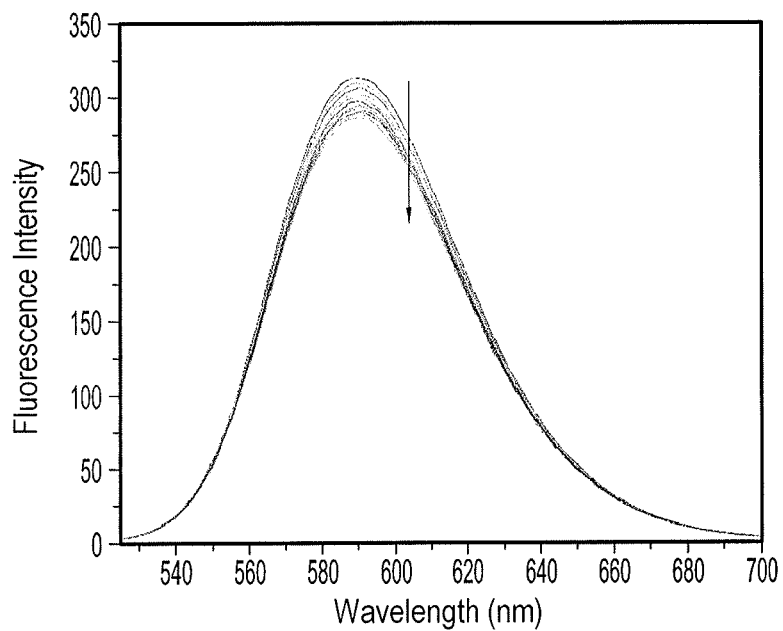
FIG. 17A are fluorescence emission spectra resulting from titration of EtBr and CT-DNA with the RAQA complex of FIG. 1A, the EtBr-DNA complex being excited at 471 nm and emission spectra being recorded from 525-700 nm, the concentration of the RAQA complex ranging from $0-50.0 \times 10^{-6}$ mol dm$^{-3}$.
Figure 17B:
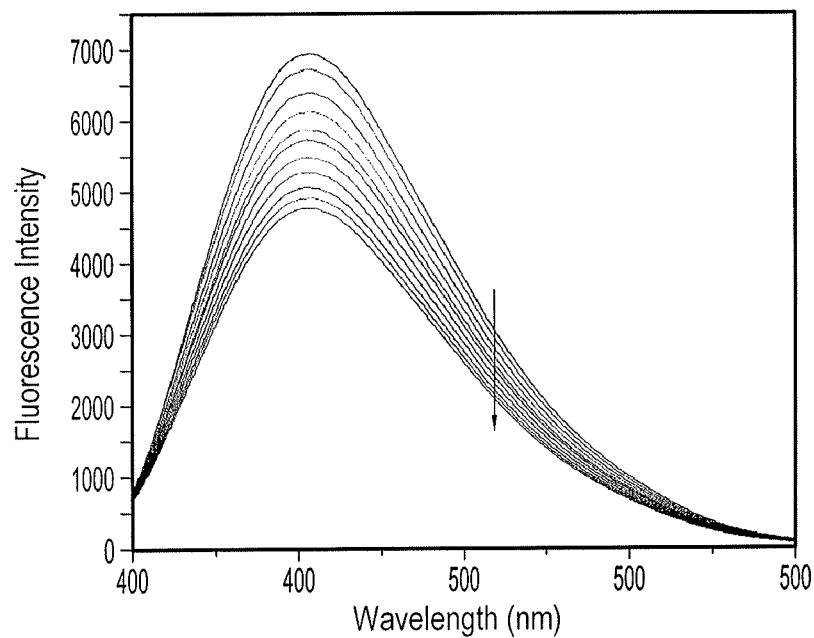
FIG. 17B is fluorescence emission spectra resulting from titration of CT-DNA and DAPI (groove binder) complex with the RAQA complex of FIG. 1A, the DAPI-DNA complex being excited at 338 nm and emission spectra being recorded from 400-600 nm, the concentration of the RAQA complex ranging from $0-50.0 \times 10^{-6}$ mol dm$^{-3}$.

Referring to FIG. 17A, the fluorescence intensity of EtBr in the presence of calf thymus DNA (CT-DNA) was almost unaffected by the RAQA complex. However, as shown in FIG. 17B, there is a considerable decrease in the intensity of DAPI in the presence of CT-DNA, which means the site of interaction between CT-DNA and the RAQA complex is minor groove (see FIGS. 15, 16, 17A-B).

Figure 18:
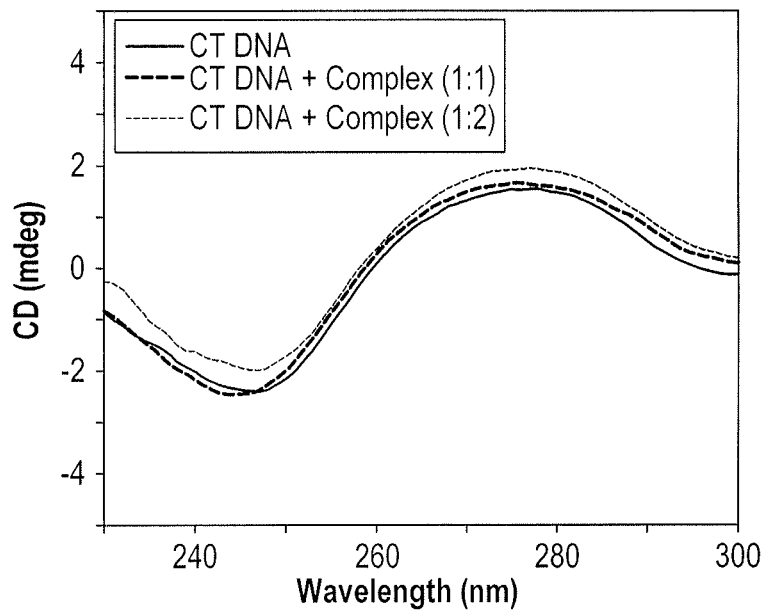
FIG. 18 is the CD (circular dichroic) spectra of CT-DNA in absence and presence of the RAQA complex of FIG. 1A, the concentration of DNA being taken as $50.0 \times 10^{-6}$ mol dm$^{-3}$.

As shown in FIG. 18, there was not much change in the ellipticity of CT-DNA, which means that the interaction was taking place in the minor groove.

Example 4

Antimicrobial Activity of RAQA Complex

MIC (minimum inhibitory concentration) was determined for the RAQA complex against the test bacteria *C. violaceum* CV12472 and *P. aeruginosa* PAO1. The RAQA complex inhibited growth against both pathogens. The MIC was found to be 100 μg/ml for *C. violaceum* CV12472 and 200 μg/ml for *P. aeruginosa* PAO1.

Figure 19:
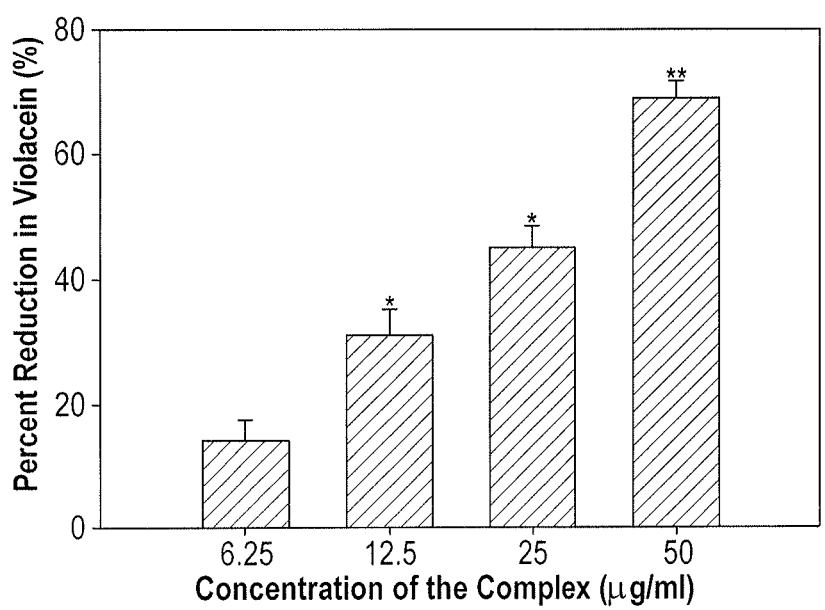
FIG. 19 is a chart showing quantitative assessment of violacein inhibition in *C. violaceum* ATCC 12472 by sub-MICs (sub-minimum inhibitory concentrations) of the RAQA complex of FIG. 1A, all of the data being presented as a mean±standard deviation *, $p \leq 0.05$, **, $p \leq 0.005$.

Violacein (purple pigment) production in *Chromobacterium violaceum* is a quorum sensing (QS) regulated function, and its production is coordinated by the CviIR-dependent QS system. In the present example, RAQA inhibited violacein production in wild-type *C. violaceum* 12472 strain in a dose-dependent manner without affecting the growth of the bacteria. Maximum reduction of 67% was recorded at 50 μg/ml, while at lower concentrations (6.25-25 μg/ml), a 14-45% decrease in violacein was observed (see FIG. 19).

Opportunistic human pathogen *P. aeruginosa* integrates ΔHL-dependent signaling with 4-quinolone dependent quorum sensing. Therefore, the las, rhl, and pqs quorum-sensing systems of *P. aeruginosa* regulate the production of several extracellular virulence factors, such as elastase, alkaline protease, motility, exopolysaccharide and pyocyanin.

Figure 20:
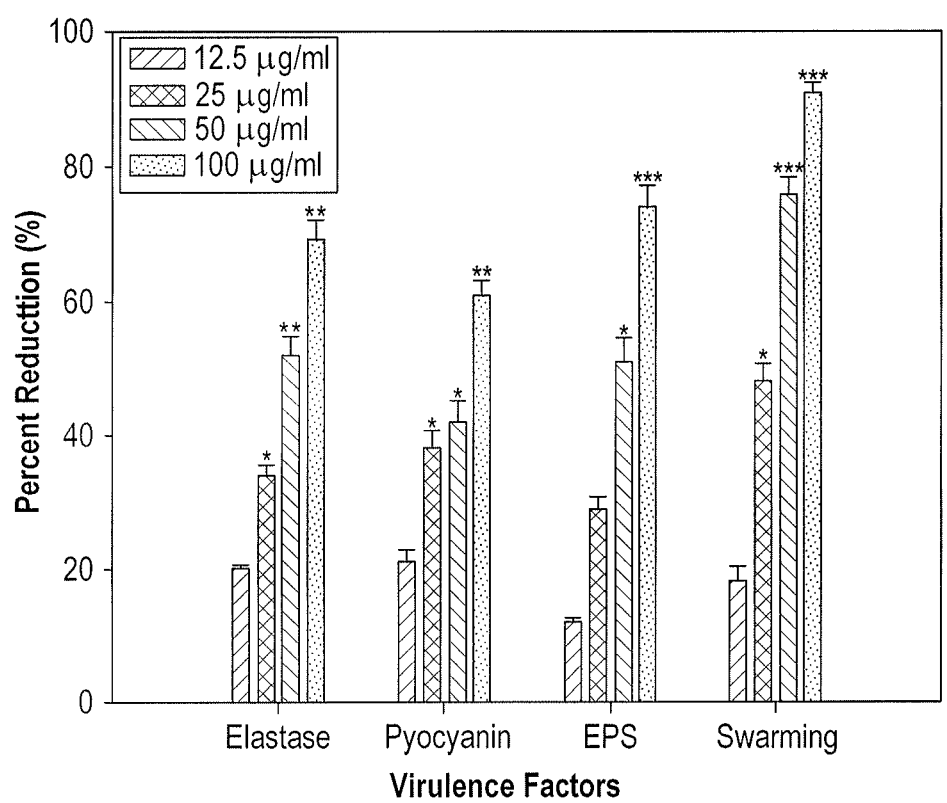
FIG. 20 is a chart showing the effect of sub-MICs of the RAQA complex of FIG. 1A on the QS-regulated (quorum sensing-regulated) virulence factors of *P. aeruginosa*, strain PAO1, all of the data being presented as a mean±standard deviation *, $p \leq 0.05$, , $p \leq 0.005$ *, $p \leq 0.001$.

The effects of sub-inhibitory concentrations of the RAQA complex on virulence factors of *P. aeruginosa* PAO1 are depicted in FIG. 20. A statistically significant decrease in LasB elastase activity was observed in the culture supernatant of PAO1 treated with sub-MICs of RAQA. A minimum of 20% inhibition was observed when PAO1 was cultured with the RAQA complex at a 12.5 μg/ml concentration, and a maximum of 69% inhibition was observed at a 100 μg/ml concentration of the extract.

Elastase enzyme enhances the growth and invasiveness of the pathogen by degrading the structural components of the infected tissue. In this example, the RAQA complex demonstrated concentration-dependent inhibition of elastase in PAO1, as shown in FIG. 20. QS regulates production of blue-colored pyocyanin. Pyocyanin and its precursor, phenazine-1-carboxylic acid (PCA), cause neutrophil apoptosis and impair neutrophil-mediated host defenses. The RAQA complex at sub-lethal concentrations exhibited a considerable decrease in pyocyanin production by PAO1. Maximum reduction of 61% in pyocyanin production was recorded at the highest tested concentration (100 μg/ml), followed by 42%, 38%, and 21% at 50, 25, and 12.5 μg/ml concentrations, respectively (see FIG. 20).

Figure 21A:
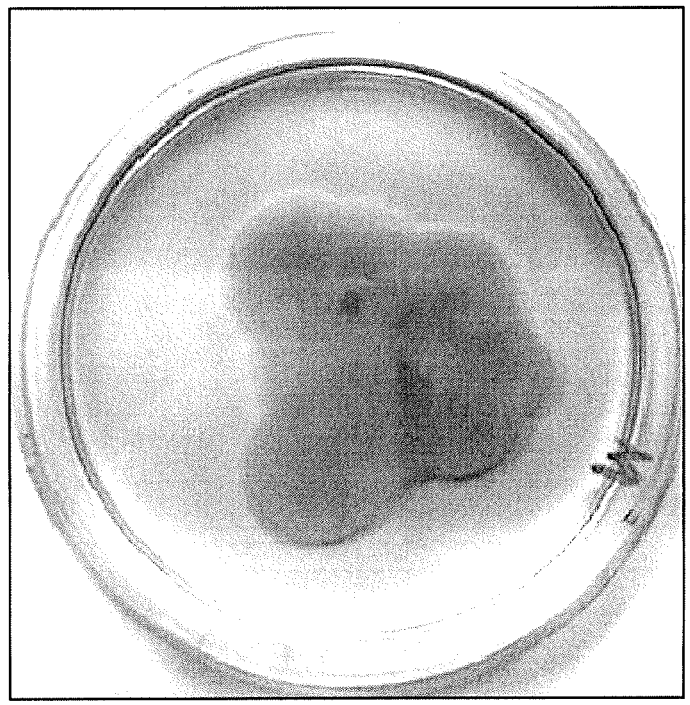
FIG. 21A is a cell culture of *P. aeruginosa*, strain PAO1 showing swarming migration of PAO1.
Figure 21B:
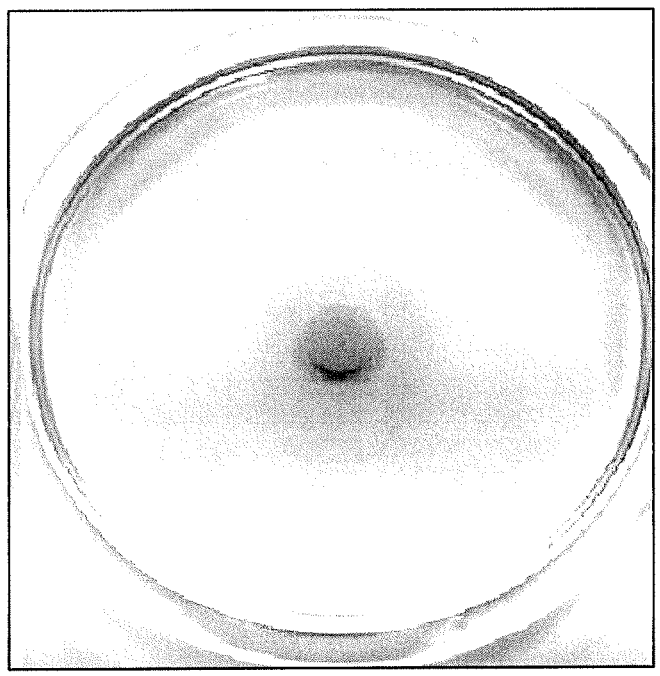
FIG. 21B is a cell culture of *P. aeruginosa*, strain PAO1 showing a significant reduction in swarming migration of PAO1 after treatment with 100 µg/ml of the RAQA complex of FIG. 1A.

Swarming motility and exopolysaccharide production by *P. aeruginosa* plays a vital role in the initiation, maturation, and maintenance of the biofilm architecture. Therefore, any interference with the motility and exopolysaccharide production is bound to effect the biofilm formation by the pathogen. In the present study, treatment of PAO1 with sub-MICs of the RAQA complex showed significantly reduced exopolysaccharide production (designated EPS in FIG. 20). The RAQA complex (12.5-100 μg/ml) demonstrated inhibition in exopolysaccharide production to the level of 12-74%. Similarly, swarming migration of PAO1 was also impaired considerably (18-91%) after treatment with test concentrations of the RAQA complex, shown quantitatively in the chart of FIG. 20 and qualitatively in the cell cultures of FIGS. 21A and 21B.

Figure 22A:
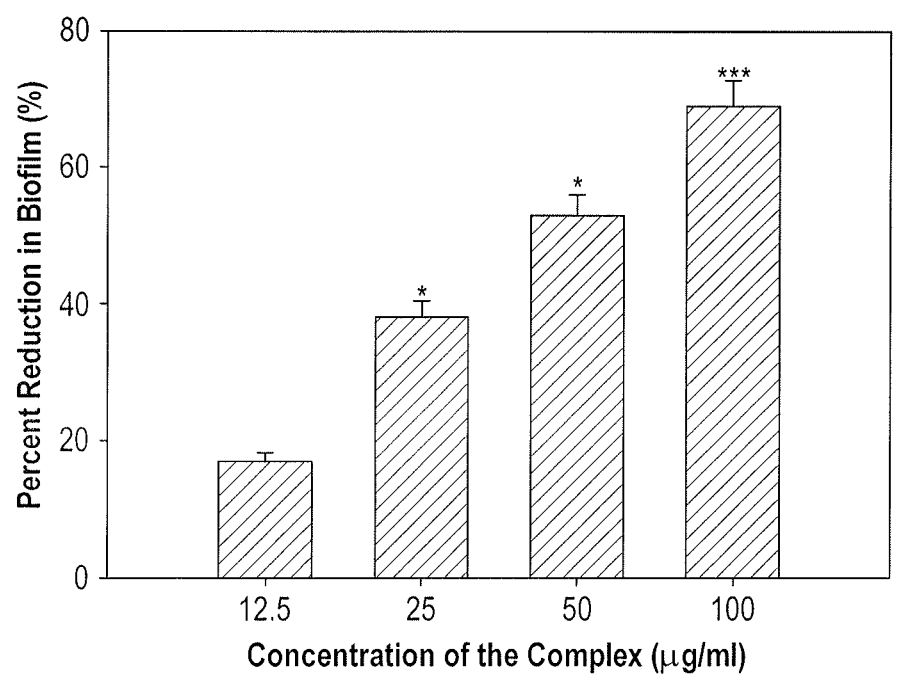
FIG. 22A is a chart showing percentage reduction in biofilm formation by *P. aeruginosa*, strain PAO1 after treatment with the RAQA complex of FIG. 1A at concentrations of 12.5 µg/ml, 25 µg/ml, 50 µg/ml, and 100 µg/ml, respectively.
Figure 22B:
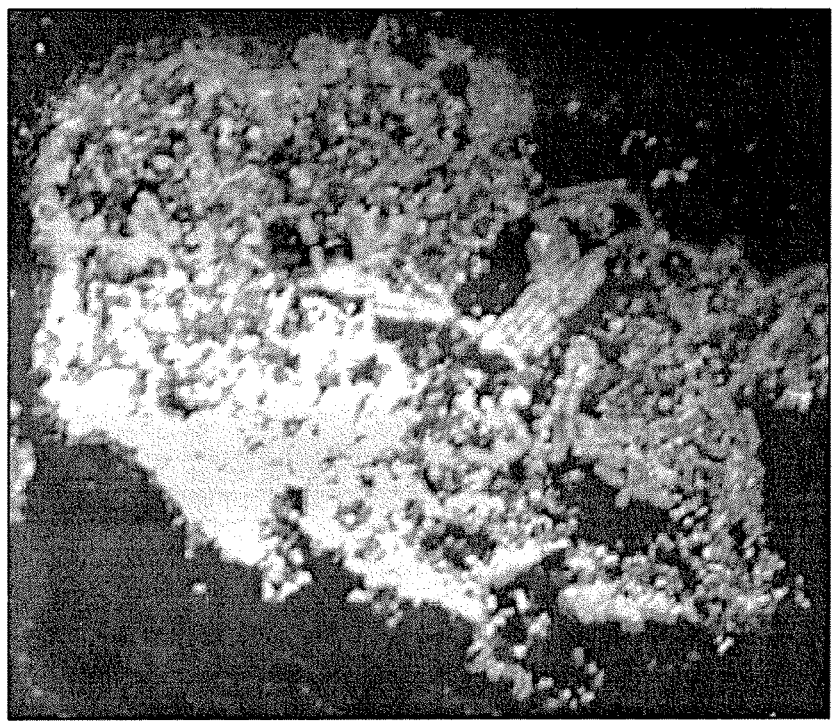
FIGS. 22B and 22C are acridine orange stained confocal laser scanning microscopy (CLSM) micrographs of untreated *P. aeruginosa* PAO1 biofilm formation and biofilm formation after treatment with 100 µg/ml of the RAQA complex of FIG. 1A, respectively.
Figure 22C:
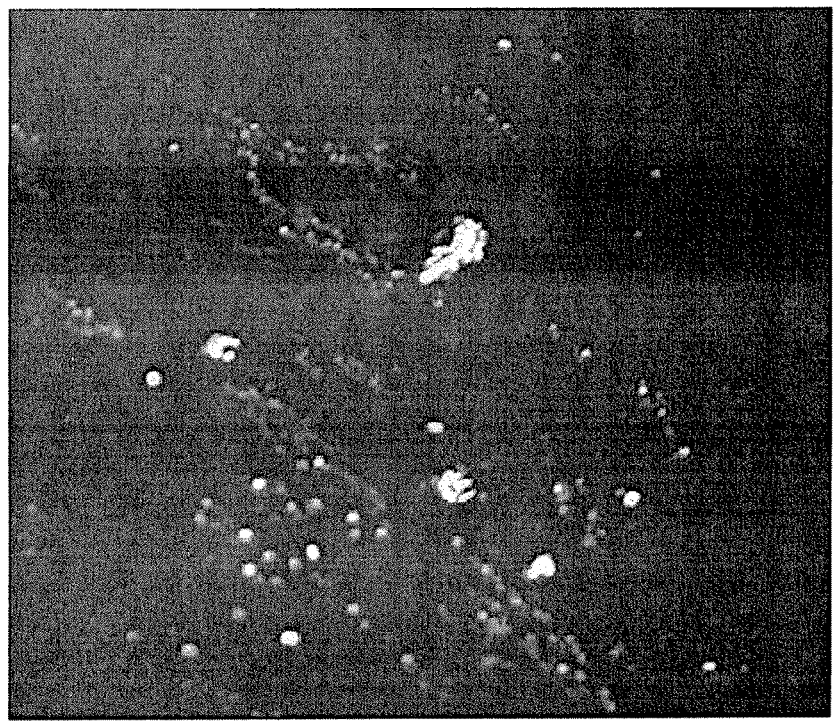

Biofilm is a drug resistant complex aggregation of microorganisms and is a key factor in the pathogenesis of *P. aeruginosa*. Biofilms are the cause of severe persistent infection and are considered as one of the potential drug targets to combat drug-resistant chronic infections. The RAQA complex showed 17%, 38%, 53%, and 69% decrease in the biofilm forming ability of PAO1 at the respective concentrations of 12.5, 25, 50, and 100 g/ml of the complex, as shown quantitatively in the chart of FIG. 22A and qualitatively in the biofilms of FIGS. 22B and 22C.

In summary, the anti-quorum and DNA cleaving agent is a ruthenium coordination compound (or coordination complex) having the formula:

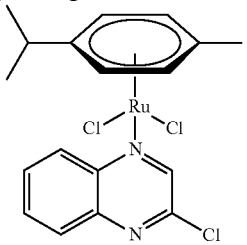

The compound is easily prepared by mixing 2-chloroquinoxaline with dichloro-($\eta^6$-p-cymene) ruthenium(II) dimer in an organic solvent and refluxing for 2-6 hours, followed by slow evaporation. Spectroscopic studies show that the compound binds to proteins, such as albumin, and has an anti-quorum sensing effect on bacteria, disrupting or interfering with inter-bacterial communication to inhibit the formation of biofilm and inhibit bacterial virulence without attacking the cell, thereby probably avoiding the drug resistance bacteria show towards antibiotics. Spectroscopic and docking studies also show that the agent binds to calf thymus DNA, probably by intercalation of the planar arene with the stacking pairs of DNA, probably binding in the minor groove, and docking studies suggest similar binding to topoisomerase. It is believed that the agent cleaves the DNA, e.g., at the N7 base pair of guanine, due to a hydrolytic mechanism due to the labile nature of the Ru—Cl bonds, suggesting exchange of Cl— anions with water. The binding and docking studies, with the availability of a DNA cleaving mechanism, suggest potential use as an anticancer or antitumor agent.

It is to be understood that the anti-quorum and DNA cleaving agent is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An anti-quorum and DNA cleaving agent, comprising a ruthenium coordination complex having a p-cymene ligand and a chloroquinoxaline ligand wherein the ruthenium coordination complex has the formula:

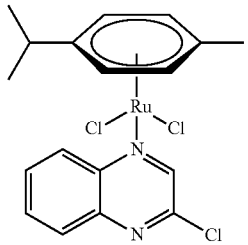

2. The anti-quorum and DNA cleaving agent according to claim 1, wherein the chlorine bonds directly to ruthenium are labile.

3. An antibacterial pharmaceutical, comprising an active compound having the formula:

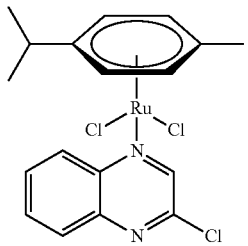

or a pharmaceutically acceptable salt thereof.

4. A method of synthesizing the ruthenium coordination complex according to claim 1, comprising the steps of:
dissolving 2-chloroquinoxaline in a solvent system to obtain a ligand solution; and
complexing the ligand solution with an alcoholic solution of p-cymene ruthenium under stirring at a prescribed temperature for a prescribed time to obtain a uniformly dispersed ruthenium complex wherein the prescribed temperature is between 75° C. and 80° C. and the prescribed time is 6-8 hours.

5. The method of synthesizing the ruthenium coordination complex according to claim 4, further comprising the steps of:
filtering the uniformly dispersed ruthenium complex;
evaporating the solvent slowly to obtain crude crystals of the ruthenium complex;
recrystallizing the crude crystals with methanol and dichloromethane to obtain purified ruthenium complex; and
drying the purified ruthenium complex under vacuum to obtain a crystalline ruthenium complex having the formula:

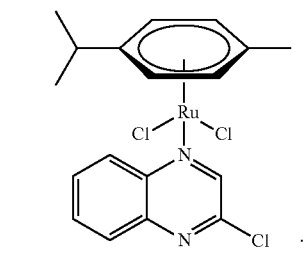

* * * * *

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: DNA dodecamer

<400> SEQUENCE: 1
cgcgaattcg cg                        12